United States Patent [19]
Iyer et al.

[11] Patent Number: 5,916,750
[45] Date of Patent: Jun. 29, 1999

[54] MULTIFUNCTIONAL LINKING REAGENTS FOR SYNTHESIS OF BRANCHED OLIGOMERS

[75] Inventors: Rajkumar Siva Iyer, Dublin; Sheng-Hui Su, San Ramon; Anita Inamdar, Sunnyvale; Krishan L. Kalra, Danville, all of Calif.

[73] Assignee: BioGenex Laboratories, San Ramon, Calif.

[21] Appl. No.: 08/780,725

[22] Filed: Jan. 8, 1997

[51] Int. Cl.[6] .......................... C12Q 1/68; C07D 413/00
[52] U.S. Cl. .................................................. 435/6; 544/83
[58] Field of Search ..................... 435/6; 544/83

[56] References Cited

U.S. PATENT DOCUMENTS 3,574,520  4/1971  Aldrich ..................................... 8/115.6
5,571,677  11/1996  Gryaznov ..................................... 435/6

*Primary Examiner*—Scott W. Houtteman
*Attorney, Agent, or Firm*—James C. Weseman, Esq.; The Law Offices of James C. Weseman

[57] ABSTRACT

Reagents capable of forming branched oligomers with monomeric units are disclosed, together with oligomers incorporating such reagents, kits containing such reagents and methods for use of such reagents in forming oligomers with monomeric units. The present reagents can advantageously be used to introduce multiple labels or reporter molecules onto oligomers such as oligonucleotides and oligopeptides. In particular, non-nucleosidic phosphoramidites based on 1,3,5-tris(2-hydroxyethyl)cyanuric acid are disclosed. Multiply-labeled, branched DNA oligomer probes constructed using these phosphoramidite reagents showed increased signal intensity relative to singly-labeled oligomer probes.

26 Claims, 5 Drawing Sheets

MULTIFUNCTIONAL LINKING REAGENTS FOR SYNTHESIS OF BRANCHED OLIGOMERS

TECHNICAL FIELD

The present invention relates generally to the use of reagents to link monomeric units in oligomers, and, more particularly, to such reagents capable of forming branched (ramified) oligomers.

BACKGROUND OF THE INVENTION

In both research applications and clinical diagnosis, it is considered desirable to link various monomeric units to form oligomeric structures. Examples of such structures include oligonucleotides, oligopeptides and the like.

For example, a known technique for determining the presence of a target nucleotide sequence in either RNA or DNA is to perform a nucleic acid hybridization assay. In such an assay, a nucleotide probe, typically an oligonucleotide, is selected having a nucleotide sequence complementary to at least a portion of the target nucleotide sequence. Typically, the probe is labelled to provide a means whereby the presence of the probe can be readily detected.

When the labelled probe is exposed to a sample suspected of containing the target nucleotide sequence, under hybridizing conditions, the target sequence will hybridize with such a labelled probe. The presence of the target sequence in the sample can then be determined qualitatively or quantitatively, usually after separating hybridized and non-hybridized probes and determining the presence and/or amount of the labelled probe which hybridized to the test sample.

Prior methods for linking a label to a nucleotide probe have generally utilized a single label attached to a nucleosidic monomeric unit, and then incorporated one or more of the nucleosidic monomeric units into the probe. For example, analogs of dUTP and UTP containing a biotin moiety have been chemically synthesized and incorporated into polynucleotides [24]. Such biotin-labelled nucleotides may then be incorporated into nucleic acid probes of biological or synthetic origin.

Other methods for labelling nucleotide probes have been proposed which allow labels to be randomly linked to nucleotides in a nucleotide oligomer. Numerous proposals have been made for incorporating multiple modified nucleosides or non-nucleosidic monomeric units into oligonucleotides with a view towards enhancing the detectability of the labelled probe and the target nucleotide sequence. In addition, it has been considered desirable to provide a means for attaching multiple labels to a single monomeric unit in an oligonucleotide probe.

However, it has been demonstrated that use of many such labelled nucleotides in a probe can reduce the stability of the hybrid formed with a target nucleotide sequence, particularly when multiple labels are present. Such reduced hybrid stability has been demonstrated for nucleic acid probes of biological origin possessing multiple biotin moieties, for synthetic oligonucleotides possessing multiple fluorescein labels, as well as for synthetic oligonucleotides possessing biotin and fluorescein labels.

In addition, derivatives of nucleoside linking phosphate groups have been disclosed, the nucleophilic moiety of which can be labelled following their incorporation into an oligonucleotide. However, such compounds, being based on nucleoside derivatives, would be expected to exhibit some of the disadvantages discussed above for nucleoside-based derivatives.

More recently, 2-amino-1,3-propanediol structures have been used to label oligonucleotides with reporter groups [6].

A number of methods to incorporate multiple reporter molecules into oligonucleotides have been described [1–8]. These utilize linear addition of labeled phosphoramidites or analogs. Since only one label is added per synthesis cycle, the number of labels that can be incorporated is limited.

Other methods for the introduction of multiple amino groups involve the use of polylysine—oligonucleotide conjugates [9–10]. These methods require the use of a combination of solid-phase peptide and oligonucleotide chemistries, a considerable disadvantage.

As one means of introducing multiple labels, as well as providing other beneficial characteristics, the production of "branched" nucleotide oligomers has been proposed. Phosphoramidites that introduce "branched" structures having two 5' ends into the nascent oligomer allow the addition of labels exponentially. For "n" synthesis cycles, the number of labels added is $2^n$. Several non-nucleosidic branching phosphoramidites are known [11–18]. These non-nucleosidic phosphoramidites are based on linear, acyclic alkanetriols.

A nucleosidic branching phosphoramidite based on a modified deoxycytidine derivative has been successfully used in nucleic acid hybridization assays [11, 19–22].

Many of the phosphoramidites used for "branching" have the inherent disadvantage that they introduce additional centers of chirality into the final structure. This disadvantage is overcome by the use of an achiral non-nucleosidic phosphoramidite [23]. In this case, phosphoramidite synthesis is a multi-step process and its use requires modification of standard DNA synthesis protocols.

Thus it is considered desirable to provide multifunctional reagents which demonstrate high coupling efficiency and thus provide higher yields of labelled oligomer.

Furthermore, it is also considered desirable to provide a class of such reagents for use in forming nucleotide oligomers which permit the resultant oligomers to hybridize with efficiencies approaching those of oligomers which contain only native nucleosidic monomeric units.

It is also considered desirable to provide such a reagent which is also capable of use in non-nucleotidic oligomers, such as in oligopeptide oligomers.

It is further considered desirable to provide such reagents which permit the use of standard synthetic chemistries.

DISCLOSURE OF THE INVENTION

The present invention provides reagents capable of linking monomeric units to form ramified oligomers, said reagents comprising compounds of the formula:

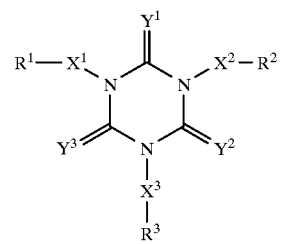

wherein

Each of $R^1$, $R^2$ and $R^3$ is independently selected from the group consisting of hydrogen, blocking groups, capping groups, labels, and groups of the formula (a)

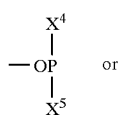

or (b)

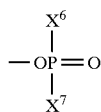

wherein
  $X^4$ is halogen or substituted amino,
  $X^5$ is alkyl, alkoxy, aryloxy, or a cyano derivative thereof,
  $X^6$ is halogen, amino or O, and
  $X^7$ is alkyl, alkoxy or aryloxy, or may be H only if $X^6$ is O, with the proviso that at least one of $R^1$, $R^2$ and $R^3$ is not hydrogen;
  Each of $X^1$, $X^2$, and $X^3$ is independently selected from the group consisting of compounds of the formula

where r is an integer at least 1, each X is independently C or O, and each C can independently be substituted or unsubstituted, saturated or unsaturated, and $Y^4$ is selected from the group consisting of, O, S, NH, N=N and a direct bond linking $X_r$ with $R^1$, $R^2$, or $R^3$; and Each of $Y^1$, $Y^2$, and $Y^3$ is independently O or S. By virtue of the symmetrical, multi-functional aspect of the present reagents, they can be used to form branching patterns in the resultant oligomers, as well as to incorporate multiple labels or otherwise desirable functionalities into the oligomers, utilizing conventional automated synthetic chemistries and protocols. In addition, the present reagents are achiral and, due to their size and rigidity, the reagents reduce the difficulties associated with steric hindrance.

Also provided in the present invention are intermediates useful for producing such reagents, oligomers incorporating such reagents, kits containing such reagents and methods for use of the reagents in forming ramified oligomers and in detecting analytes.

DETAILED DESCRIPTION OF THE INVENTION

Figure 1A:
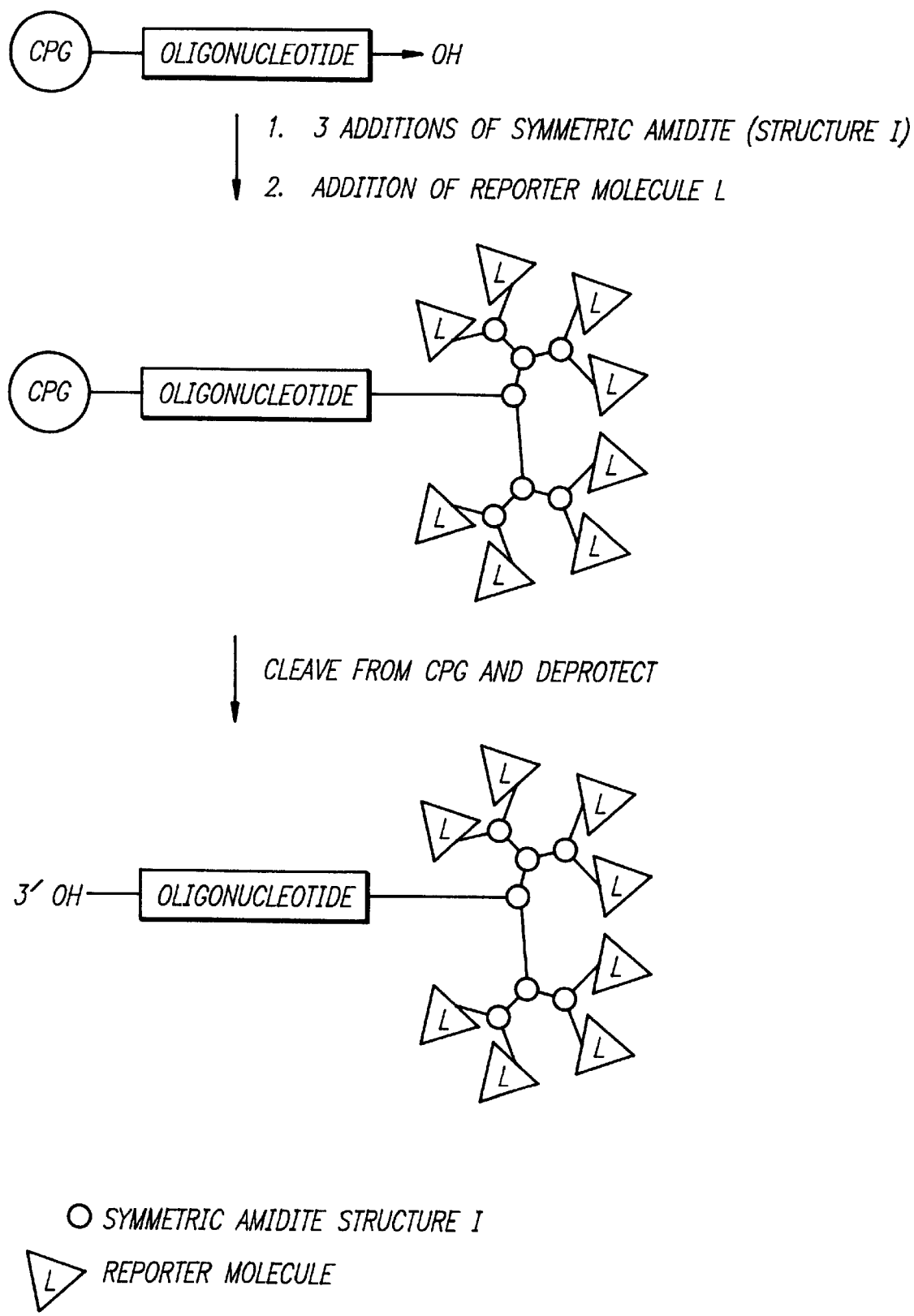
FIGS. 1A and 1B are graphic representations of selected schemes for the preparation of ramified oligomers in accordance with certain aspects of the present invention, in which FIG. 1A portrays a scheme for the preparation of a "fork" structure for the inclusion of, e.g., multiple labels, and FIG. 1B portrays a scheme for the preparation of a "comb" structure for the inclusion of, e.g., multiple labels.

The present invention provides reagents capable of linking monomeric units to form ramified oligomers, said reagents comprising compounds of the formula:

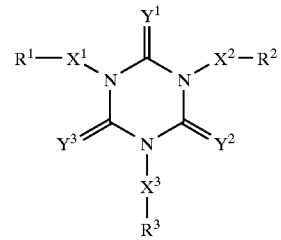

wherein
  Each of $R^1$, $R^2$ and $R^3$ is independently selected from the group consisting of hydrogen, blocking groups, capping groups, labels, and groups of the formula:

(a)

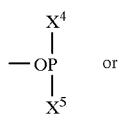

or (b)

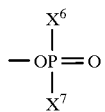

wherein
  $X^4$ is halogen or substituted amino,
  $X^5$ is alkyl, alkoxy, aryloxy, or a cyano derivative thereof,
  $X^6$ is halogen, amino or O, and
  $X^7$ is alkyl, alkoxy or aryloxy, or may be H only if $X^6$ is O, with the proviso that at least one of $R^1$, $R^2$ and $R^3$ is not hydrogen;
  Each of $X^1$, $X^2$, and $X^3$ is independently selected from the group consisting of compounds of the formula:

where r is an integer at least 1, each X is independently C or O, and each C can independently be substituted or unsubstituted, saturated or unsaturated, and $Y^4$ is selected from the group consisting of O, S, NH, N=N and direct bond linking $X_r$ with $R^1$, $R^2$, or $R^3$; and Each of $Y^1$, $Y^2$, and $Y^3$ is independently O or S.

It will be readily apparent that the present reagents provide a symmetrical, multifunctional linking unit which can easily be adapted to link any of the monomeric units of interest in biological systems, such as nucleotides and amino acids. Even with a variety of substituent groups, the cyclic central moiety of the present reagents presents a basic level of symmetry which proves useful as the degree of branching of the resultant oligomer increases. In certain embodiments, the degree of symmetry is enhanced, for example, by selecting $Y^1$, $Y^2$ and $Y^3$ to be identical atoms, and further increased by selecting $X^1$, $X^2$ and $X^3$ to be similar groups, or at least have the same value for "r". Under such conditions, it will be recognized that the relative positions of $R^1$, $R^2$ and $R^3$ are substantially interchangeable, and the discussion of the function of each separate group should be understood with this feature in mind.

In addition, because of the symmetry and multifunctional aspect of the present reagents, it will readily be appreciated that, by appropriate selection of $R^1$, $R^2$ and $R^3$, a oligomer incorporating such reagents will possess branching points, which can be used, for example, to add one or more new chains of monomeric units, an increased number of labels or other functional moieties, additional reagents in accordance with the invention, and the like.

In addition, the present reagents are achiral, so that oligomers incorporating the reagents will not thereby be rendered stereoisomeric. Stereoisomerism can result in oligomers which either broaden the peaks or resolve separately under electrophoresis, thus complicating gel purification and/or detection.

Due to their size and rigidity, the present reagents reduce the difficulties associated with steric hindrance. Particularly in multiple label oligomers, or oligomers with complex branching patterns, steric hindrance can significantly reduce the efficiency of synthesis or hybridization, rendering the reagent too costly or inefficient and thus negating the benefits of the amplification effects sought to be achieved by multiple labels.

These and other features of the present reagents will be described in greater detail below.

Use of the Reagents as Non-nucleosidic Linking Groups

The usefulness of the present reagents can be described in part by reference to their ability to serve as non-nucleosidic linking groups for the synthesis of ramified oligonucleotide oligomers. However, this description should not be construed as a limitation on the use of the reagents for the synthesis of other oligomeric structures.

In the disclosure of the reagents as non-nucleosidic units for producing oligonucleotide oligomers, the following terms will have the indicated meanings unless a contrary meaning is otherwise apparent from the context in which the term is used.

As used herein, the term "nucleotide" is taken to mean a subunit of a nucleic acid consisting of a phosphate group, a five carbon sugar and a nitrogen-containing base, and the term "nucleoside" is a subunit consisting of the linked sugar and base. The terms are also taken to include analogs of such subunits.

As used herein, the term "nucleotide oligomer (or oligomer)" is taken to mean a chain of nucleotides linked by phosphodiester bonds, or analogs thereof.

As used herein, the term "nucleotide oligomer (or oligomer) containing non-nucleosidic monomers" is taken to mean an oligomer comprised of nucleoside units together with non-nucleosidic monomeric units linked by phosphodiester bonds, or analogs thereof.

In such an aspect, the present invention provides a non-nucleosidic reagent which can be coupled synthetically with nucleosidic monomeric units to produce a defined sequence nucleotide oligomer with a backbone comprised of nucleosidic and non-nucleosidic monomeric units.

In certain embodiments of reagents of the formula first provided above,

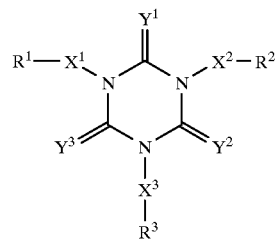

$R^1$ and $R^2$ are typically substitutent groups which are intended to be removed to facilitate linkage with other units in the backbone structure of a nucleotide oligomer containing non-nucleosidic monomers. As such, $R^1$ and $R^2$ are generally selected from the group consisting of hydrogen, blocking groups and capping groups. Commonly, such blocking groups will be acid-labile, base-stable blocking groups, and such capping groups will be acyl capping groups. Such blocking groups are well known in the art, and include, for example, triphenylmethyl compounds, and alkoxy derivatives thereof, such as dimethoxytrityl (DMT) groups. In addition, the use of blocking groups which require distinct deblocking treatments, e.g., acid-stable, base-labile blocking groups, such as the esters of levulinic acid (LEV), either separately or in combination with the acid-labile, base-stable blocking groups, permits controlled, sequential deblocking to provide greater versatility in the synthesis of ramified oligomers.

In one aspect of the invention, the group identified as $R^1$ is a substituent group which is intended to facilitate linkage with nucleosidic monomeric units, and the group identified as $R^2$ is a substituent group which is intended to facilitate linkage with other functional moieties, and other functional groups, which may be desired to be included in a nucleotide oligomer containing non-nucleosidic monomers. Such groups will commonly include labels and other reporter moieties. By way of example, $R^1$ can be DMT or LEV, and $R^2$ can be DMT, LEV, or a label, most commonly attached by means of a linking group.

In the above-mentioned embodiments of the present reagents, $R^3$ is a substituent group which is intended to facilitate linkage with other units in the backbone structure of a nucleotide oligomer containing non-nucleosidic monomers, or $R^3$ will form a bond to solid supports and the like. Typically, such linkage will be accomplished by automated methodologies, such as automated DNA/RNA synthetic protocols. As such, $R^3$ is generally selected from the group consisting of phosphodiesters, phosphotriesters, phosphites, phosphoramidites, H-phosphonates, alkyl-phosphonates, and phosphorothioates. Such groups are well known in the art, and include, for example, groups of the formula:

(a)

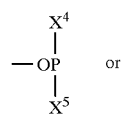

or

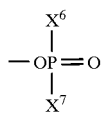
(b)

wherein $X^4$ is halogen or substituted amino, $X^5$ is alkyl, alkoxy, aryloxy, or a cyano derivative thereof, $X^6$ is halogen, amino or O, and $X^7$ is alkyl, alkoxy or aryloxy, or may be H only if $X^6$ is O, or $R^3$ is a bond, either directly or through an intermediate group, to a solid support. In order to accommodate routine nucleic acid synthetic chemistries, $R^3$ will commonly be a phosphoramidite (typically cyanoethyl or O-methyl) or an H-phosphonate, or linked to a solid support, such as controlled pore glass (CPG), often by way of a linking moiety such as long chain alkyl amine (LCAA). As mentioned previously, in embodiments of the reagents having a high degree of symmetry, the relative spatial positions of $R^1$, $R^2$ and $R^3$ should be considered freely interchangeable.

In certain embodiments of the present reagents, each of $Y^1$, $Y^2$, and $Y^3$ is independently selected from the group consisting of O and S. Such groups primarily serve to enhance the rigidity and symmetry of the core of the reagents, so that the selection of the particular atom or group is largely a matter of convenience. For example, by selecting $Y^1$, $Y^2$, and $Y^3$ as O, the commonly available cyanuric acid moieties can serve as convenient and inexpensive starting materials to produce reagents in accordance with the invention.

Further, in the present reagents, the groups identified as $X^1$, $X^2$, and $X^3$ serve, at least in part, to maintain proper intramolecular distances in the non-nucleosidic reagent when it functions as a monomeric unit. Such groups enable the use of bulky labelling moieties, such as biotin for example, while minimizing the obstacles created by steric hindrance. As such, each of $X^1$, $X^2$, and $X^3$ is independently selected from the group consisting of compounds of the formula:

where r is an integer at least 1, each X is independently C or O, and each C can independently be substituted or unsubstituted saturated or unsaturated, and $Y^4$ is selected from the group consisting of O, S, NH, N=N and a direct bond linking $X_r$ with $R^1$, $R^2$, or $R^3$, although other atoms, or groups of atoms, could also serve in this capacity. In addition, as mentioned above, a wide range of acceptable groups provides the ability to select convenient and inexpensive starting materials. For example, where $Y^1$, $Y^2$, and $Y^3$ are O, by selecting each of $X^1$, $X^2$, and $X^3$ as $(CH_2)_2$—O, the commonly available chemical 1,3,5-Tris(2-hydroxyethyl)cyanuric acid (readily available, e.g., as product no. 30,900-1 from Aldrich Chemical Co., St. Louis, Mo.) can serve as the starting material to produce reagents in accordance with the invention.

In addition, as it is desirable in certain embodiments to extend these groups, i.e. where r is greater than 3, it will ordinarily be convenient to utilize inexpensive and readily available compounds to perform this task. For example, the use of ethylene glycol-type spacers/linkers, e.g. polyethylene glycol, will often facilitate the synthesis of such extended analogs. While this will result in a repetitive —$C_2O$— unit, it will readily be appreciated that the use of this grouping is not required, but is largely a matter of expediency.

It will also be appreciated that the $R^1$, $R^2$ and $R^3$ groups of the reagents will include linking groups and/or bonds to adjacent monomeric units (either nucleosidic or non-nucleosidic) or to solid supports, such as glass beads, e.g. controlled pore glass (CPG), microbeads, resins, polymers such as polystyrene, membranes, nicrotiter plates, and the like, particularly when the reagents have been incorporated into dimeric or oligomeric structures.

Use of the Reagents as Non-peptidic Linking Groups

The present reagents will also find use as non-peptidic linking groups for the synthesis of ramified oligopeptides. Although such reagents will share numerous features in common with the above-described non-nucleosidic reagents, certain modifications will clearly be desirable for the reagents to efficiently function in this regard. For example, the blocking and capping groups used as $R^1$, $R^2$ and $R^3$ will be selected to be compatible with conventional peptide synthesis chemistries, most commonly solid-phase peptide synthesis.

Solid-phase peptide synthesis is the stepwise synthesis of a polypeptide chain attached to an insoluble polymeric support; retaining the chemistry used in solution while greatly simplifying the purification procedure without loss of product. Synthesis proceeds from the carboxyl terminus to the amino terminus of the polypeptide.

The carboxyl group of each successive amino acid monomeric unit is activated by one of several strategies, and is then coupled with the amino terminal group of the nascent chain. The α-amino group of the monomeric unit will have been temporarily protected in order to block peptide bond formation at this site, and then deprotected at the beginning of the next synthesis cycle. In addition, reactive side groups on the amino acid monomeric unit are typically protected with permanent protecting groups, such as capping groups. The polypeptide oligomer is extended by repeating the synthesis cycle until the desired oligomer is obtained.

The identity of the amino blocking group determines both the synthetic chemistry employed and the nature of the side chain protecting groups. The most commonly used amino blocking groups are FMOC (9-fluorenylmethoxycarbonyl) and t-BOC (tert-butyloxycarbonyl). FMOC side chain protection is generally provided by ester, ether and urethane derivatives of tert-butanol, while the corresponding t-BOC protecting groups are ester, ether and urethane derivatives of benzyl alcohol. The latter are usually modified by the introduction of electron-withdrawing halogens for greater acid stability. Ester and ether derivatives of cyclopentyl or cyclohexyl alcohol are also employed.

The FMOC protecting group is base-labile, and is usually removed with a base such as 20% piperidine in N,N-dimethylformamide. At the end of the synthesis, the side chain protecting groups are removed by treatment with trifluoroacetic acid (TFA), which also cleaves the bond between the polypeptide chain and the solid support. In t-BOC chemistry, the acid-labile t-BOC protecting group is removed with a mild acid, usually dilute TFA. Hydrofluoric acid (HF) is used both to deprotect the amino acid side chains and to cleave the polypeptide from the solid support. FMOC synthesis procedures are generally preferred, as they are milder than those employed in t-BOC chemistry; the peptide chain is not subject to acid solution at each synthesis cycle, and the final deprotection and cleavage step can be performed with TFA rather than the much stronger HF acid conditions.

Thus, by selection of the desired peptide synthesis chemistry, the appropriate $R^1$, $R^2$ and $R^3$ groups will be selected as a matter of course. Similarly, in such non-peptidic reagents, $R^1$, $R^2$ and $R^3$ will ordinarily not be chosen to be a phosphate group such as is described for the non-nucleosidic reagents.

Use of the Reagents as Multifunctional Linkers

Returning to a description of the present reagents as non-nucleosidic monomers, one benefit of the invention is to provide, e.g., non-nucleosidic phosphoramidites in order to synthesize ramified nucleic acid structures allowing incorporation of multiple copies of reporter molecules on oligonucleotides, leading to signal amplification. Such phosphoramidites are compatible with automated DNA/RNA synthesis protocols.

Figure 1B:
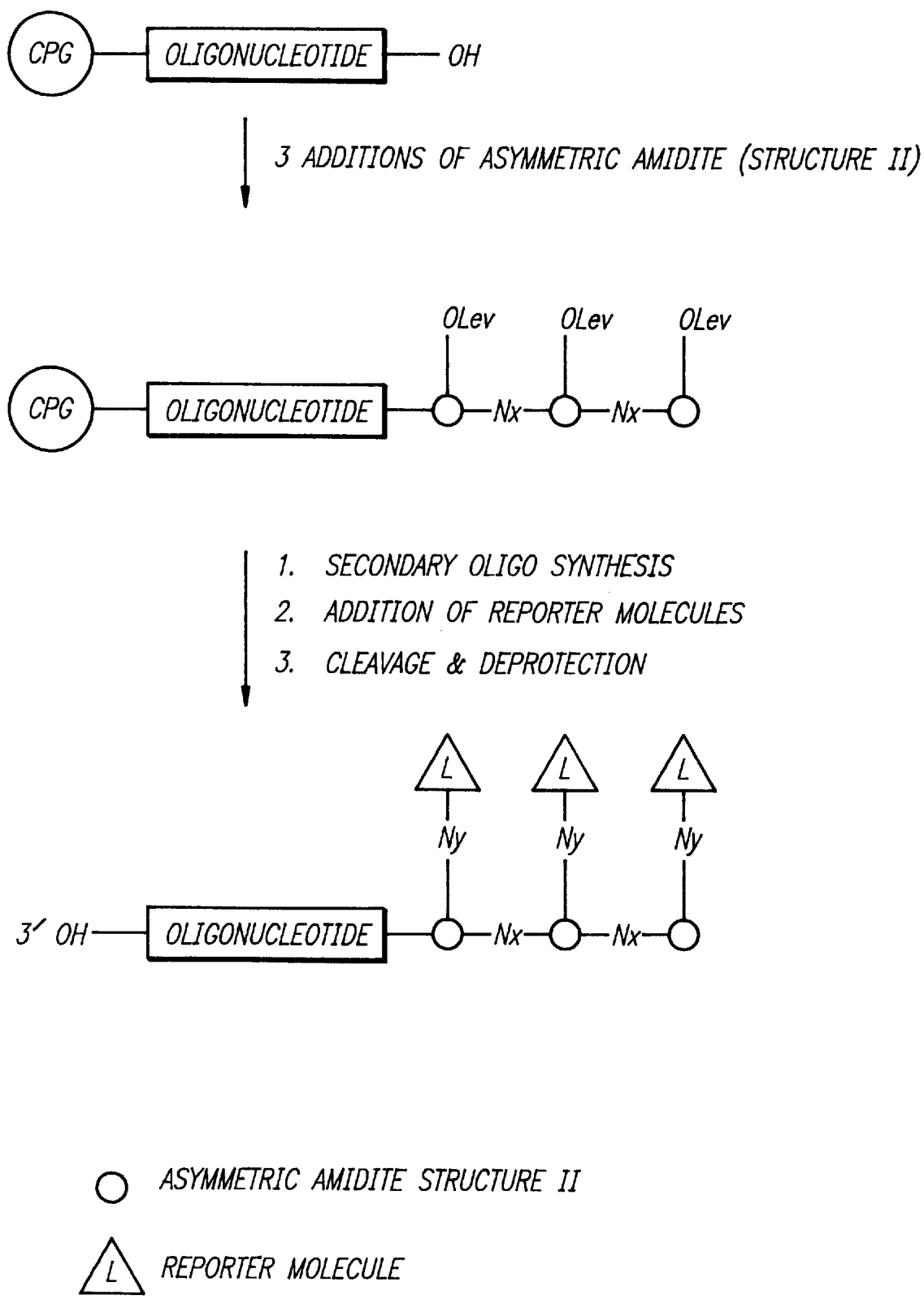

As shown in FIG. 1, and described in detail below, by selection of the appropriate reagent, and design of a compatible synthetic strategy, such ramified oligomers can provide "fork" or "comb" type structures, among others.

By way of example, non-nucleosidic phosphoramidites are provided based on the above-mentioned 1,3,5-tris(2-hydroxyethyl)cyanuric acid. These amidites can be advantageously used to synthesize multi-labeled oligonucleotides. Such oligonucleotides would increase signal intensity in target detection applications.

As depicted in structure I, two of the primary hydroxyl groups of 1,3,5-tris(2-hydroxyethyl)cyanuric acid are protected as dimethoxytrityl (DMT) ethers ($R^1$ and $R^2$) and the third primary hydroxyl group is converted to β-cyanoethyl-N,N-diisopropyl phosphoramidite ($R^3$) using standard methods.

STRUCTURE I

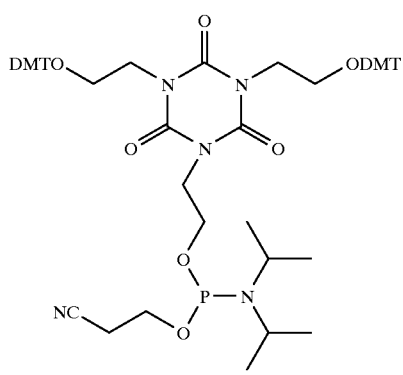

Since this amidite reagent has two substantially identical arms, it can be used during DNA synthesis to introduce identical branch points (forks) into the growing DNA structure. Further extension of synthesis can then occur at both arms simultaneously.

This reagent allows the addition of a fork (branch point) at each of multiple cycles in the nucleic acid synthesis, leading to a "ramified" DNA structure with $2^n$ 5'-termini, where n equals the number of additions of the amidite. This methodology thus provides a plurality of hydroxyl (or other functional) groups at the 5'-terminus to which reporter molecules, e.g. biotin, fluorescein, etc., can be added. Addition of reporter molecules can be carried out directly on the automated synthesis machine or post-synthetically following cleavage and deprotection of the oligonucleotide.

In structure II, one of the primary hydroxyl groups is protected as DMT ether ($R^1$), one is protected as a levulinate ester ($R^2$), and the third one is converted to CED-phosphoramidite ($R^3$):

STRUCTURE II

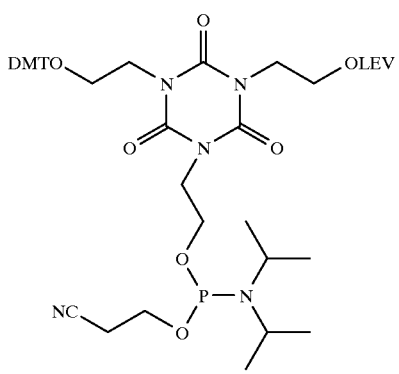

This amidite reagent would generate asymmetric branch points in the oligonucleotide chain, as the DMT and the LEV each require different deblocking procedures, and further elaboration of the chain would result in a "comb" type structure.

In structure III, one of the hydroxyl groups (at $R^2$) is attached to a functional moiety (e.g. amino, thiol, biotin, fluorescein, etc.) through a linker arm (X), and one (at $R^3$) is a phosphoramidite, H-phosphonate or attached to LCAA-CPG (collectively depicted as R). This family of reagents should find general utility analogous to other biotin or fluorescein phosphoramidites that are commercially available.

STRUCTURE III

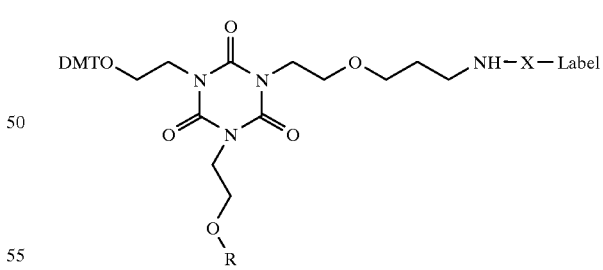

Structure IV is a dimeric version of structure I. In this version, two identical branching sub-units are linked together via a generic linker moiety (X). The advantage of this type of amidite reagent is that four identical branch points are introduced into the nucleotide oligomer per synthesis cycle.

STRUCTURE IV

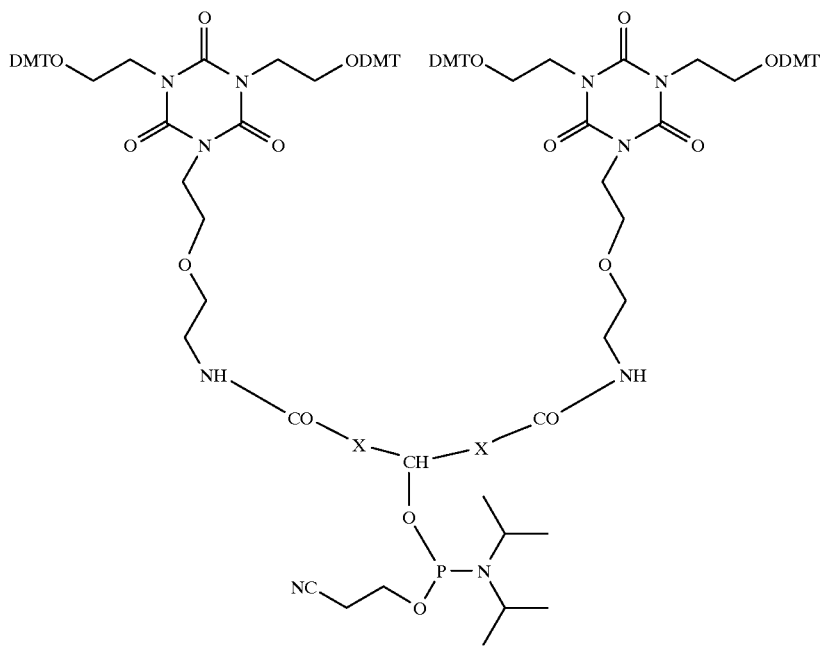

In addition, by appropriate chain extension, a oligomer incorporating the present reagents as depicted in Structure I would provide multiple oligonucleotides linked at their 3'-termini, which will be expected to prove useful in numerous labelling and probe methodologies.

Due to the chemical nature of the present non-nucleosidic reagents, they may be positioned at any desired point within the nucleotide oligomer sequence. Thus it is possible to design a wide variety of properties into oligomers which contain both nucleosidic and non-nucleosidic monomeric units. Such properties include the attachment of specific moieties herein termed "functional moieties" at any desired location within the oligomer. Such moieties can include (but are not limited to) detectable labels (including enzymatic, chromogenic, fluorogenic, radioactive, chemiluminescent, and the like), intercalating agents, metal chelators, drugs, hormones, proteins, peptides, free radical generators, nucleolytic agents, proteolytic agents, catalysts, specific binding agents (including biotin, antigens, haptens, antibodies, receptors, and the like), and other substances of biological interests, together with agents which modify DNA transport across a biological barrier (such as a membrane), and substances which alter the solubility of a nucleotide oligomer. Thus it is possible to position such labels and agents adjacent to any desired nucleotide.

In the present reagents, the rigidity of the chemical core structure also provides the desirable feature of extending the linkage group and functional moiety away from the oligomeric backbone structure, by minimizing any tendency to "fold back" via rotational freedom, and thereby substantially enhances both the coupling efficiency and the branching ability of the reagents of the present invention.

It is of course within the invention to add the functional moiety to the reagent prior to, or after, the inclusion of the reagent as a monomeric unit in an oligomer. In addition, the functional moiety can also serve as a bond to a solid support.

As discussed above, the present non-nucleosidic reagents will possess a linker functionality to which desired chemical moieties have been or can be attached, either prior to or after initiating the synthesis of the nucleotide oligomer.

In general, the techniques for linking moieties to the linker arm will be similar to the techniques known for linking labels to groups on proteins. Examples of useful chemistries include a reaction of alkyl amines with active esters, active imines, aryl fluorides or isothiocyanates, and the reaction of thiols with maleimides, haloacetyls, and the like [25–26].

As discussed above, due to the chemical nature of the present non-nucleosidic reagents, they may be positioned at any desired point within the nucleotide oligomer sequence. Thus it is possible to design a wide variety of properties into oligomers which contain both nucleosidic and non-nucleosidic monomeric units. Such properties include the attachment of specific functional moieties at any desired location within the oligomer.

Other benefits provided by the practice of the present invention include the ability to immobilize the defined sequence to a solid support by employing the linker arm functionality conjoined to a chemical moiety of the support in order to construct, for example, nucleotide affinity supports. Multiple chemical moieties can also be incorporated into the oligomer through multiple non-nucleosidic monomeric units in a particular nucleotide oligomeric sequence.

One can also provide oligomers which differ from naturally occurring polynucleotides in that they include altered activities by utilizing proteins and enzymes which act on polynucleotides. For example, the placement of the non-nucleosidic monomeric unit on the 3'-terminus of an otherwise pure polynucleotide will impart resistance to degradation by snake venom phosphodiesterases, or providing specific cleavage sites for selected nucleases.

Hybridization probes may also be constructed by interspersing hybridizable nucleosidic monomeric units and non-nucleosidic monomeric units. For example, a mixed synthesis of nucleosidic and non-nucleosidic monomers can be performed whereby a defined sequence of nucleosidic monomers are synthesized followed by a sequence of one or more non-nucleosidic monomeric units, optionally followed by a second block of a defined sequence of nucleosidic monomers.

The present invention also provides the ability to construct synthetic probes which simultaneously detect nucleotide oligomers which differ by one or more base pairs. This can be accomplished by using the non-nucleosidic reagents described herein to replace the nucleotides in a probe with non-nucleosidic monomeric units at selected sites where differences occur in the nucleotide sequence of the various target nucleotide sequences.

In selected embodiments of the invention, labelled hybridization probes are constructed as oligomers with a defined sequence comprised of nucleosidic and non-nucleosidic monomers. Such non-nucleosidic monomeric units can be grouped in a selected region or interspersed throughout the sequence of the nucleotide oligomer. The non-nucleosidic monomeric units can be chemically labelled for use in hybridization reactions.

In the present invention, the non-nucleosidic reagent is provided in a manner which permits it to be added in a stepwise fashion to produce a mixed nucleotide, non-nucleotide oligomer employing current DNA/RNA synthesis methods. Such reagents would normally be added in a stepwise manner to attach the corresponding monomeric unit to an increasing oligonucleotide chain which is covalently immobilized to a solid support. Typically, the first nucleotide is attached to the support through a cleavable ester linkage prior to the initiation of synthesis. In the present invention, the non-nucleosidic reagent can be provided conveniently linked to such solid supports, for example, to controlled pore glass (CPG), to resins, polymers such as polystyrene, and the like. Stepwise extension of the oligonucleotide chain is normally carried out in the 3' to 5' direction. Such nucleic acid synthesis methods are known [27–28].

When synthesis is complete, the oligomer is cleaved from the support by hydrolyzing the ester linkage and the nucleotide originally attached to the support becomes the 3' terminus of the resulting oligomer. Accordingly, the present invention provides both a reagent for preparing oligomers which contain a mixture of nucleosidic and non-nucleosidic monomeric units, together with methods for utilizing such reagents in the construction of such oligomers.

Typically, the present reagents will possess two coupling groups so as to permit the stepwise inclusion into a oligomer of nucleosidic and non-nucleosidic monomeric units. The first of said coupling groups will have the property that it can couple efficiently to the terminus of a growing chain of monomeric units. The second of said coupling groups is capable of further extending, in a stepwise fashion, the growing chain of mixed nucleosidic and non-nucleosidic monomers. This typically requires that the second coupling group be inactivated while the first coupling group is coupled, so as not to substantially couple at that time, the second coupling group can thereafter be activated so as to then couple the non-nucleosidic monomeric unit. The inactivation is preferably accomplished with a protecting group on the second coupling group, which can then be removed to activate the second coupling group. It is also considered to be within the scope of the invention that such "inactivation" and "activation" might be accomplished simply by changing reaction conditions (e.g. pH, temperature, concentration of reagents, and the like) with second coupling groups of suitable chemical structure which also lend themselves to inactivation and activation by such techniques.

Such coupling groups permit the adjacent attachment of either nucleosidic or non-nucleosidic monomeric units. It is considered desirable that such coupling groups operate through coupling and deprotection steps which are compatible with standard automated DNA synthesis methods.

Such methods typically require that synthesis occur unidirectionally and that all coupling cleavage and deprotection steps occur under "nonadverse conditions" that is they do not substantially adversely affect the oligomer backbone and its various components.

Thus, the present invention provides oligomers containing the present non-nucleosidic reagents, as well as methods for using such reagents in the synthesis of oligomers containing both nucleosidic and non-nucleosidic units.

In order to facilitate the use of the present reagents, kits for use in constructing oligomers can be provided to simplify practice of the method described above. The kit will typically contain a receptacle adapted to hold one or more individual reagent containers and at least a first container containing (1) a reagent in accordance with the formula:

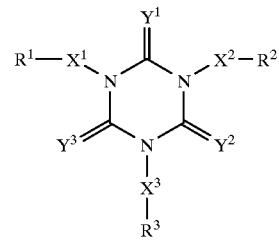

wherein
$R^1$, $R^2$, and $R^3$, $X^1$, $X^2$, and $X^3$, and $Y^1$, $Y^2$, and $Y^3$ are as previously defined. The reagent can be provided as a solution comprising a solvent and the reagent or (2) the reagent in an amount appropriate to make up the desired concentration when solvent from another container is used to fill the reagent container to a predetermined level.

In many cases, the kit will also contain at least a second container containing (1) a reagent used in the synthesis of oligomers, or (2) a reagent used in the detection of the functional moiety(s) included in the subject reagent, or containers with both such materials. Such reagents are well known in the art and require no further description here. Specific examples are given in the general examples of the invention set out below. Appropriate instructions for carrying out the method of the invention will also be included in the kit.

The following examples serve to illustrate certain preferred embodiments and aspects of the present invention and are not to be construed as limiting the scope thereof.

Experimental

In the experimental disclosure which follows, all weights are given in grams (g), milligrams (mg), micrograms (μg), nanograms (ng), or picograms (pg), all amounts are given in moles (mol), millimoles (mol), micromoles (μmol), nanomoles (nmol), picomoles (pmol), or femtomoles (fmol), all concentrations are given as percent by volume (%), proportion by volume (v:v), molar (M), millimolar (mM), micromolar (μM), nanomolar (nM), picomolar (pM), femtomolar (fM), or normal (N), all volumes are given in liters (L), milliliters (mL), or microliters (μL), and linear measurements are given in millimeters (mm), or nanometers (nm) unless otherwise indicated.

The following examples demonstrate the synthesis of reagents of the present invention, as well as their use in forming ramified oligomers with monomeric units in accordance with the invention.

EXAMPLE 1

Reagents of the present invention can be synthesized by utilizing chemical synthetic techniques well known in the art. The following protocols demonstrate the synthesis of selected compound within the scope of the present invention.

The synthetic protocol for compound 1 (Structure V) is outlined below:

Step I: Synthesis of 1,3-bis-O-(4,4'-dimethoxytrityl)-1,3,5-tris(2-hydroxyethyl)cyanuric acid 1,3,5-tris(2-hydroxyethyl)cyanuric acid (100 g, 0.38 mol, Aldrich Chemical Co.) is dissolved in 1.0 L anhydrous pyridine. To this solution is added 4,4'-dimethoxytrityl chloride (260.6 g, 0.77 mol) and the reaction mixture is stirred at room temperature overnight, under argon. The reaction is quenched by the addition of 20 mL methanol with stirring for 1 hour. After evaporating to dryness, the reaction mixture is taken up in 800 mL methylene chloride, the organic extract is washed with 5% aqueous $NaHCO_3$ solution (2×300 mL), and then dried over anhydrous sodium sulfate. Evaporation of the solvents in vacuo affords approximately 380 g of crude product, which is purified by column chromatography over silica gel, eluting with hexane:ethyl acetate (1:1, v/v), to yield approximately 153 g.

Step II: Synthesis of Phosphoramidite—Compound 1

The bis-DMT compound obtained in step I above is converted to the corresponding phosphoramidite using standard methods. Thus, 43 g of bis-DMT compound (50 mmol) is dissolved in 300 mL anhydrous methylene chloride and the resulting solution is treated with diisopropylethylamine (32 mL, 180 mmol) under argon. The resulting solution is cooled to 5°–10° C. using an ice bath. A solution of 2-cyanoethyl N,N-diisopropylchlorophosphoroamidite (21.3 g, 90 mmol) in 100 mL methylene chloride is added dropwise to the reaction mixture, and the reaction allowed to proceed at room temperature overnight. TLC analysis (hexane/ethyl acetate 7:3 v/v) will indicate the reaction to be complete. The reaction mixture is poured into 1.0 L methylene chloride, the organic layer washed with 5% sodium bicarbonate solution (2×500 mL), and then dried over anhydrous sodium sulfate. Removal of solvents by rotary evaporation will afford 63 g of crude product, which is purified by column chromatography over silica gel, and eluted with hexane/ethyl acetate/triethylamine (70:30:0.5, v/v/v) to yield 32 g of pure Compound 1.

EXAMPLE 2

The synthetic protocol for Compound 2 (Structure II) is outlined below:

Step I: Synthesis of 1-O-(4,4'-dimethoxytrityl)-1,3,5-tris(2-hydroxyethyl)cyanuricacid The mono-DMT derivative of 1,3,5-tris(2-hydroxyethyl)cyanuric acid is prepared as follows: 1,3,5-tris(2-hydroxyethyl)cyanuric acid (200 g, 0.77 mol, Aldrich Chemical Co.) is dissolved in 3.0 L anhydrous pyridine by stirring at room temperature for about 30 minutes. To this solution is added dropwise a solution of 4,4'-dimethoxytrityl chloride (52 g, 0.15 mol) in 250 mL of anhydrous pyridine. The addition is completed in about 3 hours and the reaction mixture is stirred at room temperature overnight, under argon. TLC analysis (hexane/ethyl acetate 15:85 v/v) will indicate the reaction to be complete. The crude reaction mixture is then evaporated to dryness by rotary evaporation. Residual pyridine is then removed by treating the crude mixture with toluene (2×250 mL), followed by evaporation to dryness in vacuo.

The residue thus obtained is suspended in 1.0 L methylene chloride, and unreacted 1,3,5-tris(2-hydroxyethyl)cyanuric acid is removed by filtration. The organic extract is kept aside and the filtrate is extracted twice with 1.0 L methylene chloride. The methylene chloride extracts are combined and concentrated in vacuo. The residue thus obtained is dissolved in 700 mL methylene chloride, washed with 5% aqueous $NaHCO_3$ solution (2×400 mL), and then dried over anhydrous sodium sulfate. Evaporation of the solvents in vacuo affords approximately 90 g of crude product, which is purified by column chromatography over silica gel, eluting with 3% methanol in methylene chloride, to afford approximately 41.2 g of pure product.

Step II: Synthesis of mono-Levulinate ester

The mono-DMT compound obtained in step I above is converted to the mono-levulinate ester as follows: The mono-DMT derivative of 1,3,5-tris(2-hydroxyethyl)cyanuric acid (20.0 g, 35.5 mmol), is dissolved in 350 mL of anhydrous pyridine and the resulting solution is stirred under argon. To this solution is added dropwise a solution of levulinic anhydride (7.6 g, 35.5 mmol) in 50 mL anhydrous pyridine over a period of about 3 hours. The reaction is allowed to proceed at room temperature for 4 days. TLC analysis of the reaction mixture (5% methanol in methylene chloride) indicated the presence of unreacted starting material. A solution of levulinic anhydride (1.9 g, 8.9 mmol) in 10 mL pyridine is added dropwise and the reaction is allowed to proceed for 1 day. The crude reaction mixture is then evaporated to dryness by rotary evaporation. Residual pyridine is then removed by treating the crude mixture with toluene (2×200 mL), followed by evaporation to dryness in vacuo. The residue is redissolved in 500 mL methylene chloride, the solution washed with 5% aqueous $NaHCO_3$ solution (3×400 mL), and then dried over anhydrous sodium sulfate. Evaporation of the solvents in vacuo affords approximately 24.2 g of crude product, which is purified by column chromatography over silica gel, eluting with 1% methanol in methylene chloride, to afford 6.9 g of pure mono-levulinate ester. In addition to the desired product, significant quantities of the bis-levulinate ester (about 5 g) and unreacted starting material (mono-DMT compound, 4.0 g) are also isolated.

Step III: Synthesis of the phosphoramidite compound 2

Intermediate obtained in step II above is converted to the corresponding phosphoramidite using standard methods. The mono-DMT-mono-levulinate ester of 1,3,5-tris(2-hydroxyethyl)cyanuric acid (5.0 g, 7.56 mmol) is dissolved in 150 mL methylene chloride and the resulting solution treated with 3.42 g of 2-cyanoethyl-N,N,N',N'-tetraisopropylphosphorodiamidite (1.5 equivalents, 11.34 mmol) and 646.4 mg of diisopropylamine-tetrazole salt (0.5 equivalents, 3.78 mmol). After 24 hours stirring at room temperature under argon, TLC analysis (3% methanol in methylene chloride) will indicate that the reaction is complete. The reaction mixture is diluted with 250 mL methylene chloride, washed with 5% sodium bicarbonate solution (3×300 mL), and then dried over anhydrous sodium sulfate. Removal of solvents by rotary evaporation affords 7.4 g of crude product, which is purified by column chromatography over silica gel, eluting with ethyl acetate/hexane/triethylamine (35/65/0.5, v/v/v). About 5.1 g of pure compound 2 is obtained as a sticky white solid.

EXAMPLE 3

Figure 2:
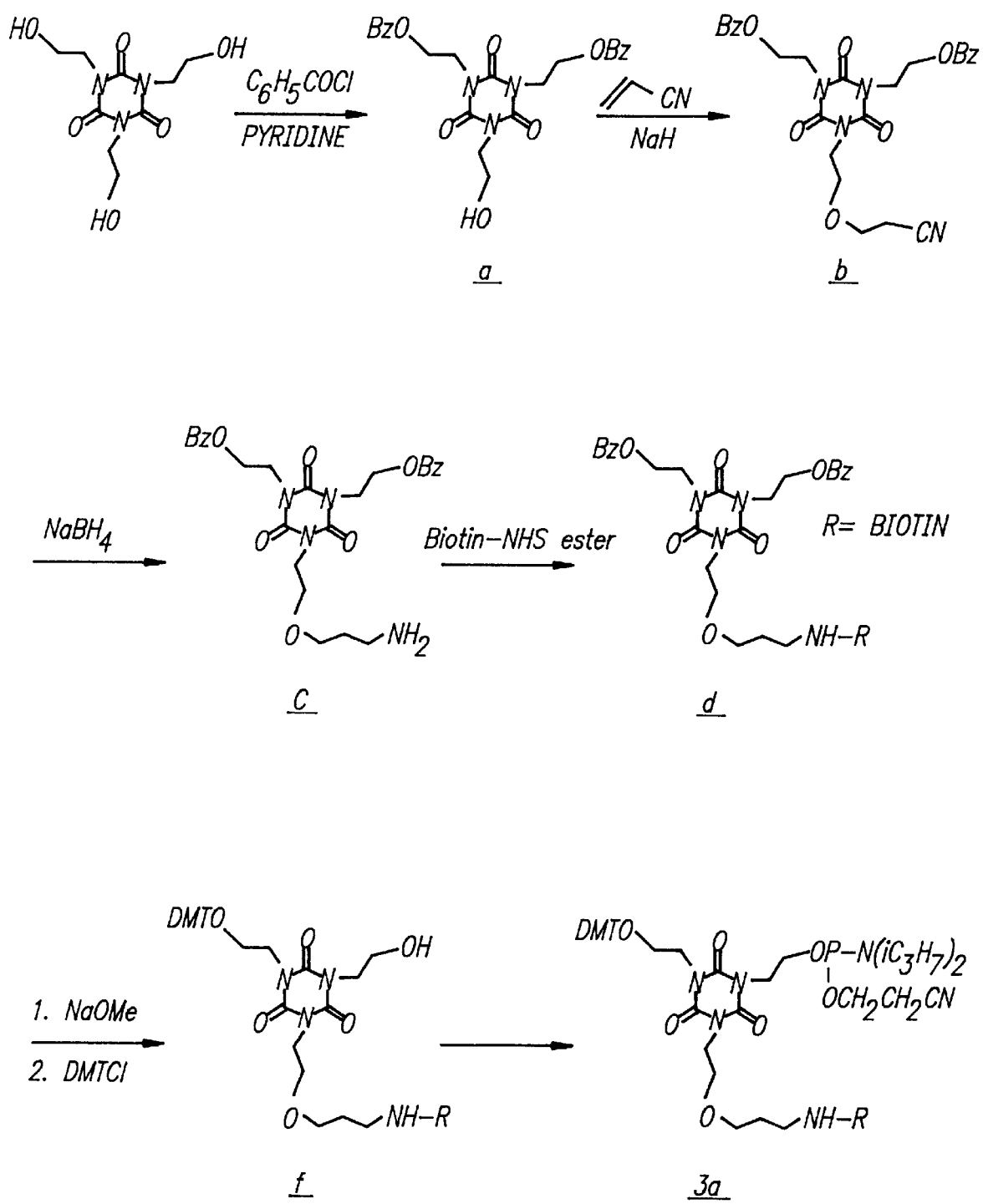
FIG. 2 schematically depicts the synthesis of selected reagents of the present invention wherein the label (R) is biotin.

The synthetic protocol for Compound 3a (Structure III; Label=Biotin) is outlined below and in FIG. 2:

Step I: Synthesis of dibenzoate ester of 1,3,5-tris(2-hydroxyethyl)cyanuric acid (a)

To an ice-cold solution of 1,3,5-tris(2-hydroxyethyl) cyanuric acid (142 g, 0.54 mol) in 1.0 L methylene chloride and 500 mL pyridine, is added dropwise 128 mL (1.09 mmol) of benzoyl chloride. The reaction mixture is stirred at room temperature overnight, whereafter TLC analysis (methylene chloride/methanol, 100:5 v/v) will indicate the reaction to be complete. The reaction is quenched by the addition of 20 mL water, followed by stirring at room temperature for 1 hour. The reaction mixture is evaporated in vacuo to afford a syrupy residue. This residue is dissolved in methylene chloride and washed with 5% aqueous $NaHCO_3$ solution (2×500 mL). The organic solution is dried over anhydrous sodium sulfate, filtered, and concentrated in vacuo to afford 254 g of crude product. This product is purified by column chromatography over silica gel, using methylene chloride/methanol (100:3, v/v) to elute the product (yield 91 g of pure dibenzoate a). The desired product is further dried under high vacuum for 2 days.

Step II: Preparation of nitrile (b)

The dibenzoate ester obtained above (76 g, 162 mmol) is suspended in 400 mL of acrylonitrile, and the resulting mixture is stirred at room temperature under argon until dissolution is complete. To this solution, sodium hydride (60% dispersion, 1.3 g, 32 mmol) is added and stirring is continued for 10 min. The reaction mixture will turn very viscous and is then diluted with anhydrous tetrahydrofuran (THF, 400 mL) to facilitate stirring. TLC analysis (methylene chloride/methanol, 100:5 v/v) will indicate the reaction to be complete after about 3 hours stirring at room temperature. The reaction is quenched by the slow addition of 4 mL conc. hydrochloric acid, followed by stirring for 30 min. The reaction mixture is then concentrated to remove acrylonitrile and THF. The resulting residue is taken up in 1.0 L methylene chloride and washed with 5% aqueous $NaHCO_3$ solution (2×500 mL). The organic solution is dried over anhydrous sodium sulfate, filtered, and concentrated in vacuo to afford 86 g of crude product. This product is purified by column chromatography over silica gel, using hexane/ethyl acetate (6:4, v/v) to elute the product (yield approximately 42 g of b).

Step III: Preparation of amine (c)

The nitrile b obtained above (40.0 g, 76.6 mmol) is dissolved in methanol (500 mL) and cobalt (II) chloride • 6 $H_2O$ (36.5 g, 153 mmol) is added. To this stirred and cooled (ice bath) solution is added sodium borohydride (28.7 g, 0.76 mol) in several portions. Stirring is continued for 1 hour and then concentrated ammonium hydroxide solution (200 mL) is added. The resulting suspension is filtered and the filtrate concentrated to remove methanol. The reaction mixture is then extracted with methylene chloride (1.2 L), the extract dried over anhydrous sodium sulfate, and then evaporated to give amine c as an oil (30.6 g). Amine c is purified by column chromatography over silica gel, using gradient elution with 5.0–8.0% methanol in methylene chloride as the eluant.

Step IV: Reaction with biotin active ester—Preparation of (d)

To a solution of amine c (8.0 g, 15.2 mmol) in 100 mL of methylene chloride, is added dropwise a solution of biotin N-hydroxysuccniimide ester (6.5 g, 17.5 mmol) in anhydrous dimethylformamide (DMF, 80 mL), followed by the addition of triethylamine (4.3 mL, 30.5 mmol) to the reaction mixture. After 1 hour at room temperature, TLC analysis will indicate that the reaction has proceeded to completion. The reaction mixture is concentrated to remove methylene chloride, and then quenched by the addition of 20 mL methanol followed by addition of 10 mL of 10% sodium carbonate solution. After stirring for 30 min, the reaction mixture is extracted with ethyl acetate (800 mL), the organic extract washed with brine (2×300 mL), and finally dried over anhydrous sodium sulfate. Evaporation of solvents in vacuo affords the title compound d (15.7 g). This crude product is purified by column chromatography over silica gel, using gradient elution with 2.5–6.0% methanol in methylene chloride to yield approximately 9.2 g.

Step V: Hydrolysis of benzoate esters—Preparation of (e)

To an ice-cold solution of d (9.0 g, 11.3 mmol) in DMF (100 mL), is added dropwise a solution of sodium methoxide in methanol (25% w/v, 9.4 mL, 43.5 mmol). The reaction is allowed to proceed at 0°–5° C. for 1 hour. The pH of the solution is then adjusted to 7.0 by the addition of 28 g Dowex 50X8-100 resin to the reaction mixture followed by stirring for 15 min. The resin is filtered off and the filtrate evaporated to remove DMF. The residue is dissolved in methylene chloride (10 mL) and the product reprecipitated from hexane (50 mL). After drying, approximately 6.7 g of product e is obtained and is used without further purification.

Step VI: Dimethoxytritylation of e—Preparation of (f)

Compound e (6.7 g, 11.3 mmol) is dissolved in 100 mL anhydrous pyridine and azeotroped to dryness. The residue is dissolved in 200 mL pyridine. To this solution is added 4,4'-dimethoxytrityl chloride (3.8 g, 11.3 mmol) and the reaction mixture stirred at room temperature overnight, under argon. The reaction is quenched by the addition of 5 mL methanol and stirred for 1 hour. After evaporating to dryness, the reaction mixture is taken up in 500 mL methylene chloride, the organic extract is washed with 5% aqueous $NaHCO_3$ solution (2×200 mL), and then dried over anhydrous sodium sulfate. Evaporation of the solvents in vacuo affords approximately 7.3 g of crude product, which is purified by column chromatography over silica gel, eluting with methylene chloride/methanol (100:4, v/v).

Step VII: Synthesis of the phosphoramidite 3a

The intermediate obtained in step VI above is converted to the corresponding phosphoramidite using standard methods. Thus, f (1.3 g, 1.5 mmol) is dissolved in 30 mL methylene chloride and the resulting solution is treated with 0.74 mL of 2-cyanoethyl-N,N,N',N'-tetraisopropylphosphorodiamidite (2.25 mmol) and 150 mg of diiospropylamine-tetrazole salt. After 15 hours at room temperature, the reaction is quenched by addition of 1.0 mL methanol. The reaction mixture is poured into 200 mL methylene chloride, the organic layer washed with 5% sodium bicarbonate solution (2×80 mL), and then dried over anhydrous sodium sulfate. Removal of solvents by rotary evaporation affords 1.9 g of crude product, which can be purified by column chromatography over silica gel, eluting with $CH_2Cl_2$/methanol/triethylamine (100:1:1, v/v/v).

EXAMPLE 4

Testing the ramified oligonucleotide probe structures.

The following examples demonstrate the detection of oligonucleotide probes constructed utilizing reagents of the present invention.

In microtiter plate assay examples, the detection is performed utilizing a streptavidin-alkaline phosphatase system employing para-nitrophenyl phosphate as substrate. Hydrolysis by alkaline phosphatase converts this substrate to a chromogen detectable at 405 nm. In assay examples following the "dot-blot" model, the chemniluminescent substrate CDPStar® (TROPIX Inc., Bedford, Mass.) is used. The light emission resulting from substrate hydrolysis is captured on X-ray film.

Three assay formats are used as examples. In the first, biotinylated oligonucleotide probes are covalently coupled to a derivatised microtiter plate. The biotin residues are then quantitated using the streptavidin detection system. These examples indicate that the branching (ramification) of the oligomer structure leads to a crowding effect, which does not promote the detection of biotin residues. The crowding effect is ameliorated by increasing the length of the branches before attachment of the biotin residues.

In the second set of examples, an unlabeled template is immobilized on a derivatised microtiter plate. The biotinylated oligonucleotide probes are allowed to hybridize to the template and then detected.

In the third set of examples, unlabeled template is immobilized on a nylon membrane. Biotinylated oligonucleotide probes are allowed to hybridize and the hybridized probes are detected using the streptavidin-alkaline phosphatase system with a chemiluminescent substrate.

The following materials are utilized in the assay examples:

1. 1-Ethyl-3-(3-dimethylaminopropyl)-carbodiimide (EDC)
2. Streptavidin-alkaline phosphatase
3. p-Nitrophenylphosphate (PNPP, chromogenic substrate for alkaline phosphatase)
4. CDPStar® (chemiluminescent substrate for alkaline phosphatase)
5. 2-Amino-1,3-propanediol (AMPD, reaction buffer for pNPP)
6. Alu consensus template (Alu-011A)
7. Alu consensus probe (ACP)
8. Biotinylated oligonucleotide structures (5'→3') (P=phosphate):

BG1004: Biotin-ACP-P BG1005: (2 Biotin)—ramified structure-ACP-P BG1007: (4 Biotin)—ramified structure-ACP-P BG1008: (4 Biotin)—(dT)$_3$-ramified structure-ACP-P BG1009: (4 Biotin)—(dT)$_5$-ramified structure-ACP-P BG1010: (8 Biotin)—ramified structure-ACP-P BG1011: (16 Biotin)—ramified structure-ACP-P BG1016: (4 Biotin)—(spacer)$_3$-ramified structure-ACP-P BG1018: (16 Biotin)—(spacer)$_3$-ramified structure-ACP-P Synthesis of multi-labeled ramified oligonucleotides.

Oligonucleotides are synthesized on a 0.2 μl scale using either an Eppendorf® D-100 DNA synthesizer or an Eppendorf® D-300 Plus DNA synthesizer. Construction of the multi-labeled oligomers is accomplished in two steps: A) synthesis of a "stem" consisting of a specific sequence of unmodified nucleotides, and B) addition of "branches" (forks) and multiple modifying groups to the stem. Synthesis of the stem is accomplished using standard DNA synthesis protocols—no changes are necessary. Construction of the branches involves the use of a 1.0 μmol RNA synthesis protocol utilizing multiple additions of phosphoramidites. The coupling time is increased to 10 minutes. Branching phosphoramidite 1, spacer amidite 9, and amino-linker phosphoramidite are all used at 0.15–0.2M concentrations. These conditions are selected recognizing that as the number of branches in the oligomer increases, steric crowding increases significantly.

Further, the number of available reactive sites increases exponentially with each addition of a branching phosphoramidite; e.g. for a 0.2 μmol scale synthesis, four sequential additions of a symmetric branching phosphoramidite yields 16×0.2=3.2 μmol of reactive functional groups. Insufficient delivery of reagents therefore results in lower coupling efficiencies and hence lower isolated product yields. These problems are overcome by increasing amidite concentrations, increasing amidite delivery, and extending coupling wait times. Commercially available spacer phosphoramidite 9 is used in order to increase the accessibility of the biotin (or other label molecules) to the detection system. Commercially available amino-modifier phosphoramidite is used in order to provide a plurality of reactive primary amino groups at the end of the oligomer probe. These primary amino groups could be used to introduce biotin, fluorescein, or other label molecules post-synthetically. Introduction of label molecules could also be carried out directly on the DNA synthesizer via the use of labeled phosphoramidites, e.g. biotin or fluorescein phosphoramidites. Following synthesis, the ramified oligonucleotides are cleaved (30 min at room temperature) and deprotected using standard DNA synthesis protocols (15 hours at 55° C. in concentrated ammonium hydroxide solution). Oligonucleotides can be purified on reversed-phase cartridges following DMT-ON synthesis (oligomer synthesis with the 5'-terminal DMT moiety intact).

Labeling of synthetic oligonucleotides with biotin.

Oligonucleotides are synthesized with terminal amine groups. The active ester of biotin, N-hydroxysuccinimide-biotin, is dissolved in dimethylformamide at a concentration of either 10 or 20 mg/mL. For each individual ramified structure, the molarity of amine groups is considered to be one. For instance, in the (8 Biotin)-labeled structure, one mole of oligonucleotide is considered equivalent to eight moles of amine groups. A 20-fold molar excess of biotin over amine groups is used in a 100 μl reaction containing 5 nmol of synthetic oligonucleotide and 10 mM sodium carbonate buffer at pH 9.0.

Coupling of oligonucleotides to microtiter plate.

This procedure is described by Rasmussen et al. (*Anal. Biochem.* 198:138, 1991). Derivatized microtiter plates containing a secondary amine are used. Condensation of the terminal phosphate group of an oligonucleotide with the secondary amine is carried out in buffer containing 0.2 M EDC, 0.01 M 1-Methylimidazole, pH 7.0, at 50° C. for 5 hours. When biotinylated oligonucleotides are coupled to the plate, the concentration of oligonucleotide is varied between 0.5 and 10 fmol/μl. When template Alu-011A is used, the lowest concentration of template is 0.1 fmol/μl.

Immobilization of template DNA to nylon membrane.

One μl of template Alu-011A of appropriate concentration (ranging from 1 pmol/μL to 1 fmol/μL) is spotted on positively charged nylon membranes (Hybond-N™, Amersham, Inc.). After air drying, the DNA is cross-linked to the membrane by exposure to short-wave WV light (254 nm) for 10 min.

Hybridization of immobilized template to oligonucleotide probes

Microtiter plate assays—For the microtiter plate assay examples, the probes are used at a concentration of 25 pmol/mL in hybridization buffer (0.15 M sodium chloride, SmM sodium phosphate buffer pH 7.0, containing 5 mM EDTA, 0.1% Tween-20, 50% formamide and 100 μg/mL salmon sperm DNA). 100 μL of hybridization buffer is added to each well of the microtiter plate. Hybridization is carried out at 42° C. for 5 hours.

Dot blot assays—Hybridization of labeled probes to the immobilized template and subsequent chemiluminescent detection were performed using the ULTRALUME® GENEBLOT™ detection kit (catalog # D201-GD, BioGenex, San Ramon, Calif. 94583). All buffers and wash solutions are used as described in the instructions for the kit.

Membranes containing the immobilized template are prewetted with about 5 mL of 2× SSPE buffer (0.3 M NaCl, 0.02 M dibasic sodium phosphate, 2mM EDTA, pH 7.4) for 1–2 minutes. The membranes are then inserted into sterile plastic tubes. The labeled probes of interest (BG1004 and BG1018) are then diluted to the appropriate concentration (2.5 pmol/mL) with hybridization buffer (0.15 M NaCl, 5 mM sodium phosphate buffer, pH 7.0, containing 5 mM EDTA, 0.1% Tween-20, 50% fonmamide, and 100 μg/mL salmon sperm DNA). The diluted probe solution (500 μL) is then added to the tube containing the membrane, and the tube placed in a hybridization oven maintained at 42° C. Hybridization is carried out at 42° C. for 1 hour with the tube containing the membranes mounted on a rotator to ensure proper mixing. After hybridization, the membranes are transferred to a wash tray. The membranes are then washed thrice for 5 minutes each time at room temperature, in about 5 mL of Wash Buffer C (containing 0.15 M sodium chloride, along with casein and 0.5% SDS). Washings are performed with gentle agitation and removal of reagents after each wash.

Detection of biotin residues.

Streptavidin-alkaline phosphatase conjugate is incubated with the support-bound biotinylated probe for 20 minutes at room temperature.

For chromogenic detection, substrate pNPP is dissolved in 0.18 M AMPD at 1 mg/mL. 100 μl of substrate is incubated with the complex of alkaline phosphatase—streptavidin—biotinylated probe. Absorbance of the colored product p-nitrophenol is measured at 405 nm in a microtiter plate reader.

In the case of the membrane assays, after hybridization and washes are completed, the membranes are incubated with 1× Label (alkaline phosphatase-conjugated streptavidin; prepared from 200× label stock and diluted with Wash Buffer C) for 20 minutes at room temperature. The membranes are then washed twice for 5 minutes each time at room temperature, in about 10 mL of Wash Buffer C, with gentle agitation. The membranes are then incubated for 5 minutes twice with gentle agitation in about 10 mL of 1× UltraLume® Buffer. For Chemiluminescent detection, membranes bearing the complex alkaline phosphotase-streptavidin-biotinylated probe-template, are incubated with substrate CDPStar® between two transparent plastic sheets and the membrane is exposed to X-ray film. The membranes are positioned on the inside of a development folder and the chemiluminescent substrate is added (200–300 μL of UltraLume® Substrate). The development folder is then exposed to X-ray film (Kodak X-Omat AR, Sigma Catalog # F-5513) for about 30–60 minutes, and the intensity of the resulting dots is compared visually.

EXAMPLE 4A

Biotinylated oligonucleotides are coupled to the derivatized microtiter plate and detected by the streptavidin-alkaline phosphatase method, as described above. Representative data are shown in Table 1.

TABLE 1

Effect of Increasing Label Density on Measured Signal Intensity

| | # of biotins | Absorbance at 405 nm | | | | | Ratio of signal at 40 min |
|---|---|---|---|---|---|---|---|
| | | 0 min | 20 min | 40 min | 60 min | 80 min | |
| A. Oligo | | | | | | | |
| BG1004 | 1 | 0.00 | 0.05 | 0.07 | 0.14 | 0.18 | 1.0 |
| BG1005 | 2 | 0.00 | 0.06 | 0.09 | 0.16 | 0.21 | 1.3 |

TABLE 1-continued

Effect of Increasing Label Density on Measured Signal Intensity

| | # of biotins | Absorbance at 405 nm | | | | | Ratio of signal at 40 min |
|---|---|---|---|---|---|---|---|
| | | 0 min | 20 min | 40 min | 60 min | 80 min | |
| BG1007 | 4 | 0.00 | 0.07 | 0.14 | 0.25 | 0.33 | 2.0 |
| BG1008 | 4 | 0.00 | 0.11 | 0.26 | 0.41 | 0.54 | 3.7 |
| BG1009 | 4 | 0.00 | 0.16 | 0.39 | 0.54 | 0.72 | 5.6 |
| BG1010 | 8 | 0.00 | 0.17 | 0.34 | 0.54 | 0.71 | 4.8 |
| BG1011 | 16 | 0.00 | 0.27 | 0.52 | 0.74 | 1.00 | 7.4 |
| B. Oligo | | | | | | | |
| BG1004 | 1 | 0.00 | 0.02 | 0.06 | 0.11 | 0.13 | 1.0 |
| BG1007 | 4 | 0.00 | 0.04 | 0.14 | 0.25 | 0.33 | 2.1 |
| BG1011 | 16 | 0.00 | 0.24 | 0.54 | 0.94 | 1.16 | 8.2 |
| BG1016 | 4 | 0.00 | 0.47 | 1.06 | 1.84 | 1.89 | 16.2 |
| BG1018 | 16 | 0.00 | 0.68 | 1.72 | 1.82 | 1.82 | 26.2 |

Figure 3A:
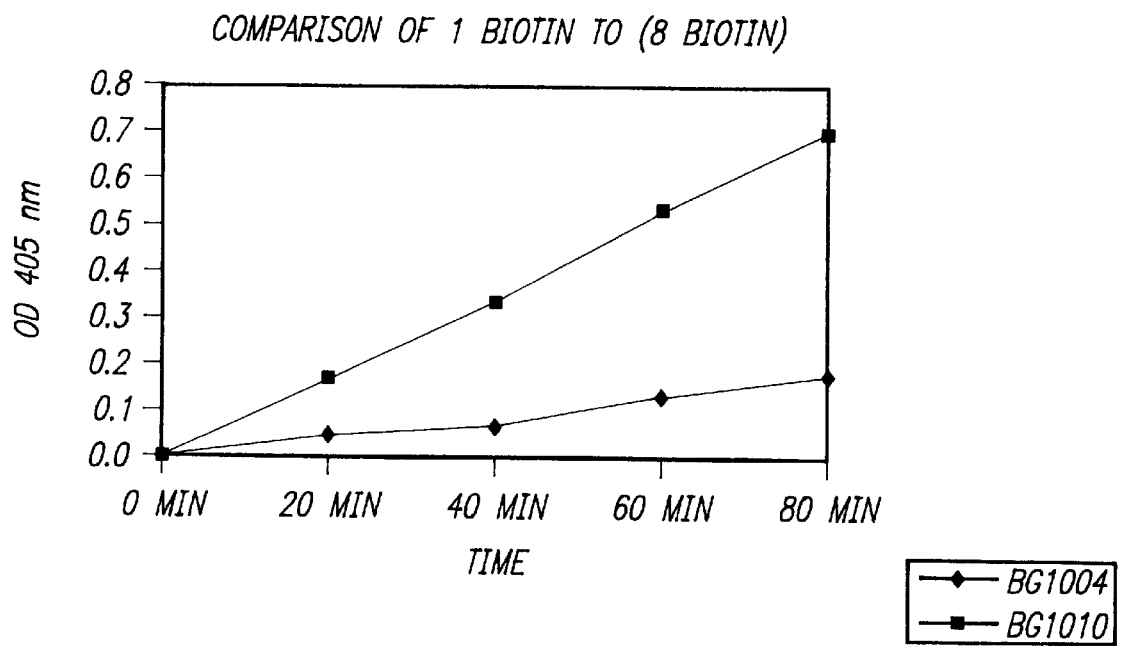
FIG. 3 is a graphic representation of the relative detectability of oligonucleotide probes in accordance with the invention containing single versus multiple labels, in which FIG. 3A compares 1 (BG1004) versus 8 (BG1010) labels per probe, FIG. 3B compares 1 (BG1004) versus 16 (BG1018) labels per probe, and FIG. 3C compares 1 (BG1004) versus 4 (BG1007) and 16 (BG1011) labels per probe (without spacer) and versus 4 (BG1016) and 16 (BG1018) labels per probe (with spacer)
Figure 3B:
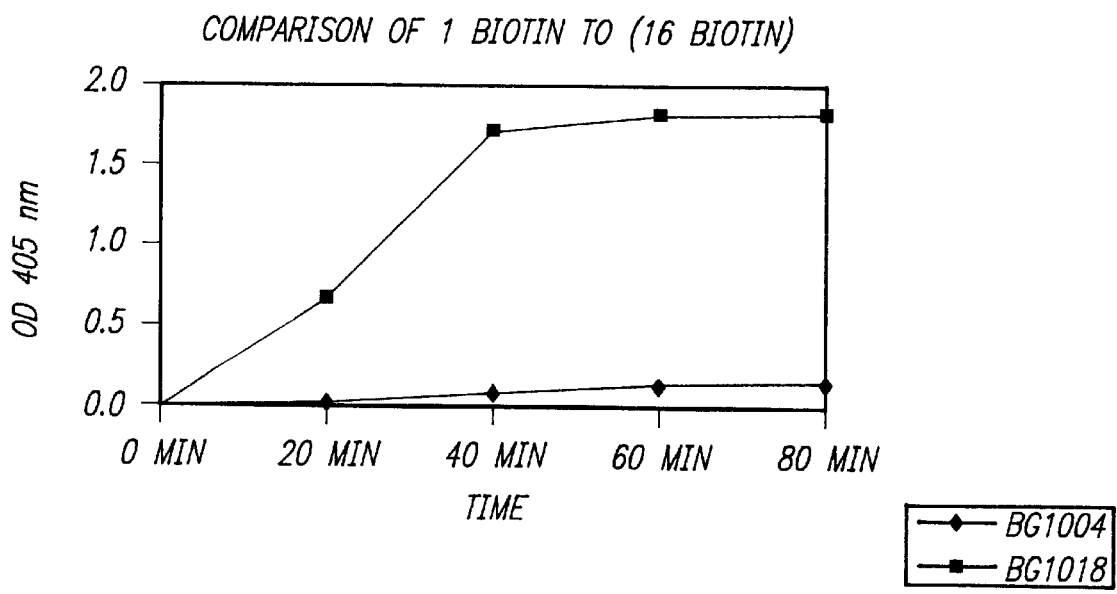
Figure 3C:
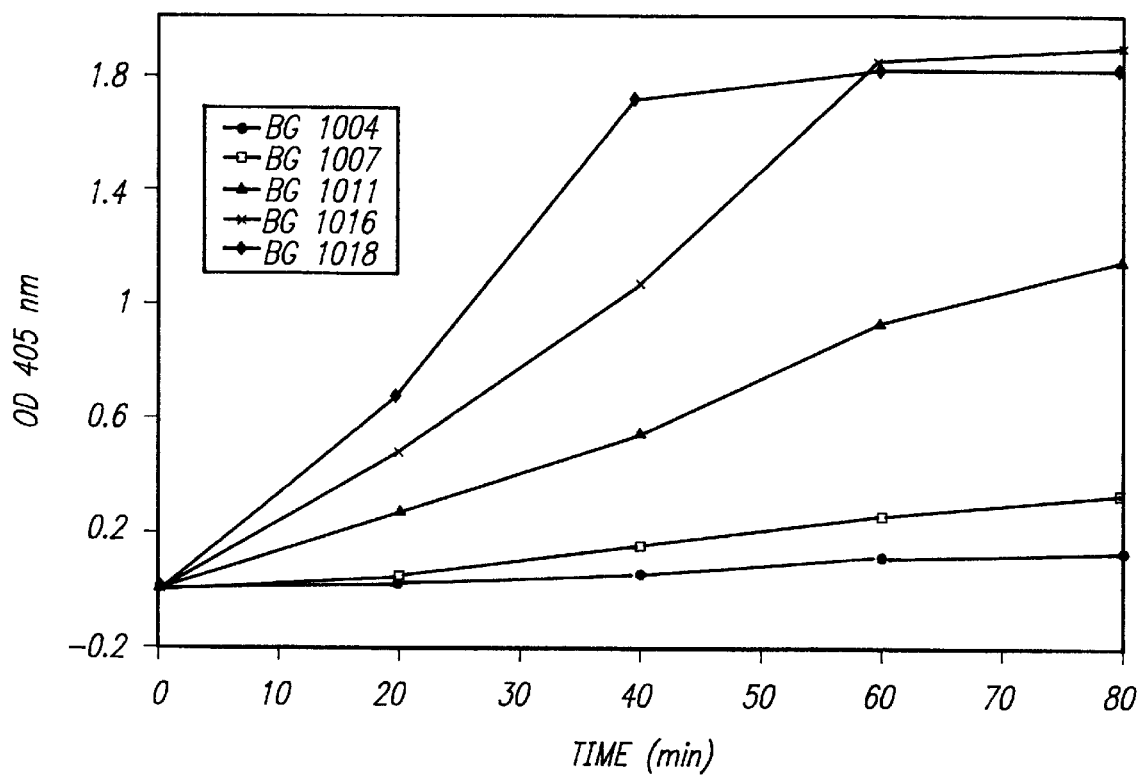

As can be seen, the (16 Biotin) oligonucleotide produces 1 log more signal than the (1 Biotin) oligonucleotide. These data are also presented graphically in FIG. 3.

EXAMPLE 4B

Microtiter plate assay: Template Alu-011A is immobilized on microtiter plates at concentrations varying from 0.1 to 10 fmol/μL. A uniform concentration of oligonucleotide probes (25 pmol/mL) is hybridized to the template. The data are presented in Table 2 and the 80 minute data shown graphically in FIG. 4.

TABLE 2

Detection Sensitivity of Probes of Increasing Label Density

| | Template concentration | | Absorbance at 405 nm | | | | |
|---|---|---|---|---|---|---|---|
| | | | 0 min | 20 min | 40 min | 60 min | 80 min |
| BG1004 | 0.10 | fm | 0.01 | 0.01 | 0.16 | 0.01 | 0.02 |
| | 0.25 | fm | 0.00 | 0.00 | 0.01 | 0.00 | 0.01 |
| | 0.50 | fm | 0.00 | 0.01 | 0.02 | 0.02 | 0.03 |
| | 0.75 | fm | −0.01 | 0.01 | 0.02 | 0.02 | 0.04 |
| | 1.0 | fm | 0.00 | 0.02 | 0.04 | 0.04 | 0.07 |
| | 2.5 | fm | 0.01 | 0.04 | 0.08 | 0.12 | 0.17 |
| | 5.0 | fm | 0.01 | 0.08 | 0.15 | 0.21 | 0.31 |
| | 7.5 | fm | 0.00 | 0.08 | 0.18 | 0.28 | 0.39 |
| | 10 | fm | 0.01 | 0.10 | 0.10 | 0.38 | 0.53 |
| BG1018 | 0.10 | fm | 0.00 | 0.01 | 0.01 | 0.01 | 0.01 |
| | 0.25 | fm | −0.01 | 0.02 | 0.06 | 0.10 | 0.15 |
| | 0.50 | fm | 0.00 | 0.05 | 0.14 | 0.21 | 0.32 |
| | 0.75 | fm | 0.00 | 0.07 | 0.20 | 0.31 | 0.45 |
| | 1.0 | fm | 0.01 | 0.14 | 0.35 | 0.52 | 0.74 |
| | 2.5 | fm | 0.02 | 0.35 | 0.82 | 1.26 | 1.75 |
| | 5.0 | fm | 0.05 | 0.59 | 1.38 | 1.80 | 1.80 |
| | 7.5 | fm | 0.08 | 0.68 | 1.76 | 1.80 | 1.80 |
| | 10 | fm | 0.05 | 0.66 | 1.55 | 1.80 | 1.80 |

Figure 4:
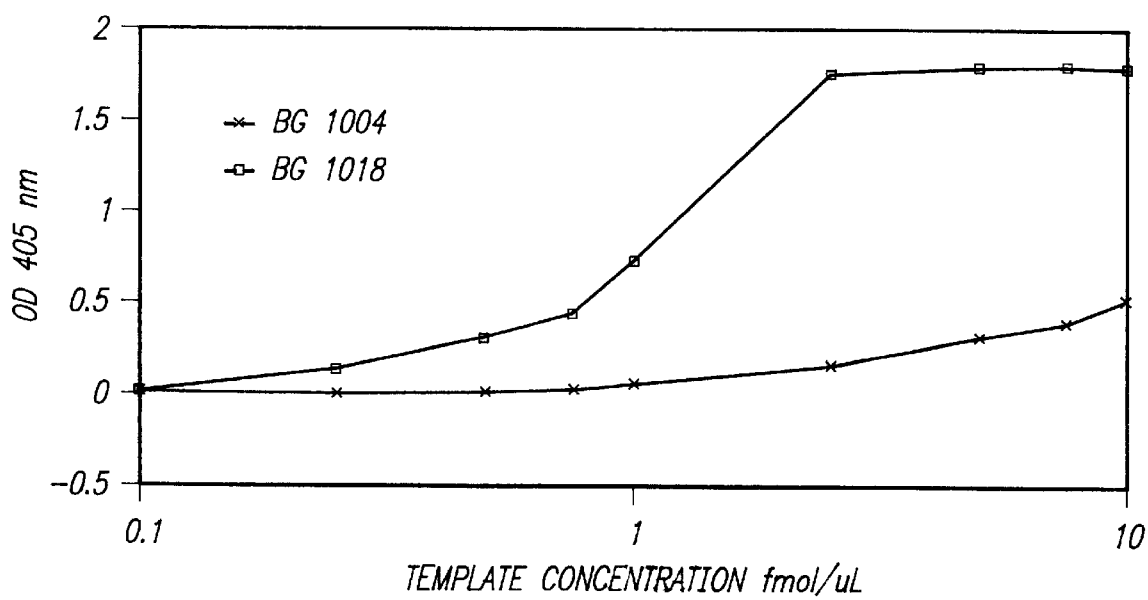
FIG. 4 graphically depicts the detection of decreasing concentrations of a target nucleic acid sequence using ramified probes (1 (BG1004) versus 16 (BG1018) labels per probe) prepared in accordance with the invention.

The results are calculated as the amount of template detected at a signal intensity of OD 405 nm=0.5 (see FIG. 4). Using the 1 Biotin oligonucleotide BG1004, this amount is 9.8 fmol/μl, whereas when the (16 Biotin) oligonucleotide BG1018 is used, 0.8 fmol/μl of template is detected. The (16 Biotin) oligonucleotide is 1 log more sensitive than the 1 Biotin oligonucleotide.

EXAMPLE 4C

Membrane assay: Template Alu-011A is immobilized on nylon membranes at amounts decreasing from 1pmol to 1fmol. Membranes are hybridized with 2.5 pmol/mL of oligonucleotide probes BG1004 or BG1018.

It appears that whereas the (16 Biotin) probe BG1018 is able to detect 5 fmol of template, in the case of 1 Biotin probe BG1004, the same signal intensity requires about 100 fmol of template.

Data from the assay examples discussed above show that the multi-labeled probe is 10 to 20-fold more sensitive than the singly-labeled probe. Higher order structures, i.e. the incorporation of more labels on a probe, will lead to a correspondingly higher signal intensity.

All publications and patent applications cited in this specification are hereby incorporated by reference as if they had been specifically and individually indicated to be incorporated by reference.

Although the foregoing invention has been described in some detail by way of illustration and example for purposes of clarity and understanding, it will be apparent to those of ordinary skill in the art in light of the disclosure that certain changes and modifications may be made thereto without departing from the spirit or scope of the appended claims.

REFERENCES

1. K. Misiura, et al. Biotinyl and phosphotyrosinyl phosphoramidite derivatives useful in the incorporation of multiple reporter groups on synthetic oligonucleotides. *Nuc. Acids Res.* 18, 4345 (1990).

2. K. Misiura, et al. A new multiple labeling method for synthetic oligonucleotides and increased sensitivity in DNA detection. *Nucleosides and Nucleotides,* 10, 671 (1991).

3. K. Misiura and M. J Gait. Phosphoramidite derivatives, their preparation and the use thereof in the incorporation of reporter groups on synthetic oligonucleotides. EPO Patent Document #00527184/EP (1995).

4. J. Y. Tang and S. Agrawal. Incorporation of multiple reporter groups on synthetic oligonucleotides. *Nuc. Acids Res.* 18, 6461 (1990).

5. S. Gryaznov, et al. An approach to the synthesis of multilabeled oligodeoxyribonucleotide probes. *Nuc. Acids Res. Symposium Series* 24, 207 (1991).

6. P. S. Nelson, et al. Oligonucleotide labeling methods 3. Direct labeling of oligonucleotides employing a novel, non-nucleosidic, 2-aminobutyl-1,3-propanediol backbone. *Nuc. Acids Res.* 20, 6253 (1992).

7. V. Zecchini, et al. Detection of nucleic acids in the attomole range using polybiotinylated oligonucleotide probes. *BioTechniques* 19, 286 (1995).

8. A. Guzaev, et al. Novel non-nucleosidic building blocks for the preparation of multilabeled oligonucleotides. *Bioconjugate Chem.* 7, 240 (1996).

9. A. Yamane, et al. Poly-labeled oligonucleotide derivative. PCT Patent Document # 04876335 (1989).

10. J. Haralambidis, et al. The preparation of polyamide-oligonucleotide probes containing multiple non-radioactive labels. *Nuc. Acids Res.* 18, 501 (1990).

11. B. Hervé, et al. Phosphoramidite reagents for the easy preparation of polylabeled oligonucleotide probes. *Nucleosides and Nucleotides* 10, 363 (1991).

12. R. Téoule, et al. Derivatives of polyhydroxylated molecules for introducing at least one ramification in an oligonucleotide. EPO Patent Document # 00451213/EP. (1994).

13. V. A. Korshun, et al. Non-nucleotide phosphoramidite reagent for non-radioactive polylabeling of oligo-and polynucleotides. *Nuc. Acids Res. Symposium Series* 24, 269 (1991).

14. S. Teigelkamp, et al. Branched poly-labeled oligonucleotides: enhanced specificity of fork-shaped biotinylated oligoribonucleotides for antisense affinity selection. *Nuc. Acids Res.* 21, 4651 (1993).

15. Anonymous—Clontech product literature. Branching phosphoramidites. *CLONTECHniques,* April (1993).

16. D. Gallagher, et al. hnproved sensitivity using branched oligonucleotide probes: chromosomal FISH analysis of bovine satellite I. *Oligotechniques* 2, 1 (1994) (Clontech Laboratories, Inc.).

17. M. J. De Vos, et al. New non-nucleosidic phosphoramidites for the solid phase multi-labeling of oligonucleotides: comb- and multifork-like structures. *Nucleosides and Nucleotides* 13, 2245 (1994).

18. M. S. Urdea, et al. Bifunctional blocked phosphoramidites useful in making nucleic acid oligomers. U.S. Pat. No. 5,359,100, (1994).

19. T. Horn and M. S. Urdea. Forks and combs and DNA: the synthesis of branched oligodeoxyribonucleotides. *Nuc. Acids Res.* 17, 6959 (1989).

20. C-A. Chang, et al. Improved methods for the synthesis of branched DNA (bDNA) for use as amplification oligomers in bioassays. *Nucleosides and Nucleotides* 10, 389 (1991).

21. M. S. Urdea, et al. Branched DNA amplification oligomers for the sensitive, direct detection of human hepatitis viruses. *Nuc. Acids Res. Symposium Series* 24, 197 (1991).

22. M. S. Urdea, et al. Improved amplified nucleic acid hybridization assays for hepatitis B virus (HBV), and synthesis of linear and branched oligonucleotide oligomers therefor. PCT Patent Document # 90 13667.

23. C. Behrens, et al. A new achiral reagent for the incorporation of multiple amino groups into oligonucelotides. *Bioorganic and Medicinal Chem. Lett.* 5, 1785 (1995).

24. P. R. Langer et al., *Proc. Nat. Acad. Sci. USA* 78:6633 (1981).

25. Means, G. M. and R. E. Feeney, "Chemical Modification of Proteins" Holden-Day Inc. (1971).

26. R. E. Feeney, *Int. J. Peptide Protein Res.* 29:145–161 (1987).

27. S. A. Narang, "Synthesis and Applications of DNA and RNA," Academic Press (1987).

28. M. J. Gait "Oligonucleotide Synthesis," IRL Press (1984).

We claim:

1. A reagent which is capable of forming a oligomer with monomeric units, said reagent comprising a compound of the formula:

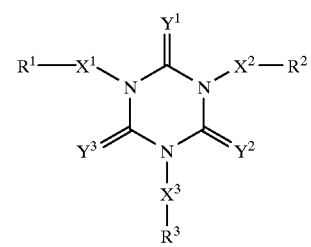

wherein

Each of $R^1$, $R^2$ and $R^3$ is independently selected from the group consisting of hydrogen, blocking groups, capping groups, labels, and groups of the formula:

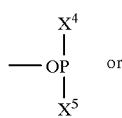

wherein

X⁴ is halogen or substituted amino,

X⁵ is alkyl, alkoxy, aryloxy, or a cyano derivative thereof,

X⁶ is halogen, amino or O, and

X⁷ is alkyl, alkoxy or aryloxy, or may be H only if X⁶ is O, with the proviso that at least one of R¹, R² and R³ is not hydrogen;

Each of X¹, X², and X³ is independently selected from the group consisting of compounds of the formula

where r is an integer at least 1, each X is independently C or O, and each C can independently be substituted or unsubstituted, saturated or unsaturated, and Y⁴ is selected from the group consisting of O, S, NH, N=N and a direct bond linking $X_r$ with R¹, R², or R³; and Each of Y¹, Y², and Y³ is independently O or S.

2. A reagent as recited in claim 1, wherein R¹ is selected from the group consisting of acid-labile, base-stable blocking groups.

3. A reagent as recited in claim 2, wherein R¹ is dimethoxytrityl.

4. A reagent as recited in claim 1, wherein R² is selected from the group consisting of acid-stable, base-labile blocking groups.

5. A reagent as recited in claim 4, wherein R² is a levulinate ester.

6. A reagent as recited in claim 1, wherein each of X¹, X₂, and X³ is —(CH₂)₂—Y⁴.

7. A reagent as recited in claim 6, wherein Y⁴ is O.

8. A reagent as recited in claim 1, wherein each of Y¹, Y², and Y³ is O.

9. A reagent as recited in claim 1, wherein R³ is selected from the group consisting of phosphodiesters, phosphotriesters, phosphites, phosphoramidites, H-phosphonates, alkyl-phosphonates, and phosphorothioates.

10. A reagent as recited in claim 1, wherein R³ comprises a bond, either directly or through an intermediate group, to a solid support.

11. A reagent as recited in claim 1, wherein
R¹ is dimethoxytrityl,
R² is dimethoxytrityl,
R³ is β-cyanoethyl-N,N-diisopropyl phosphoramidite, each of X¹, X², and X³ is —(CH₂)₂—Y⁴, where
Y⁴ is O for X¹ and X² and is a direct bond linking $X_r$ with R³ for X³, and each of Y¹, Y², and Y³ is O.

12. A reagent as recited in claim 1, wherein
R¹ is dimethoxytrityl,
R² is a levulinate ester,
R³ is β-cyanoethyl-N,N-diisopropyl phosphoramidite, each of X¹, X², and X³ is —(CH₂)₂—Y⁴, where
Y⁴ is O for X¹ and X² and is a direct bond linking $X_r$ with R³ for X³, and each of Y¹, Y₂, and Y³ is O.

13. A reagent as recited in claim 1, wherein
R¹ is dimethoxytrityl,
R² is a functional moiety attached through a linker arm,
R³ is phosphoramidite, H-phosphonate or a bond to LCAA-CPG, each of X¹, X², and X³ is —(CH₂)₂—Y⁴,
Y⁴ is O, and each of Y¹, Y₂, and Y³ is O.

14. A reagent as recited in claim 1, wherein at least one of R¹, R² and R³ comprises a functional moiety selected from the group consisting of detectable labels, intercalating agents, metal chelators, drugs, hormones, proteins, peptides, free radical generators, nucleolytic agents, proteolytic agents, catalysts, specific binding agents, agents which modify DNA transport across a biological barrier, and substances which alter the solubility of a nucleotide oligomer.

15. A dimeric reagent comprising two reagents as recited in claim 1.

16. A dimeric reagent as recited in claim 15, wherein:
each R¹ and R² is dimethoxytrityl or levulinic acid ester,
each R³ is attached either directly or by a linking group to a phosphoramidite, H-phosphonate or LCAA-CPG,
each of X¹, X², and X³ is —(CH₂)₂—Y⁴,
Y⁴ is O, and each of Y¹, Y², and Y³ is O.

17. A nucleic acid oligomer having nucleotide and non-nucleotide monomeric units, at least one of said non-nucleotide units comprising a compound of the formula:

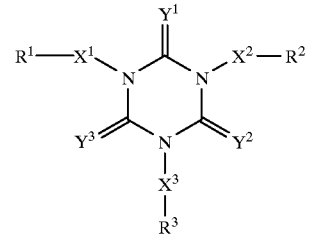

wherein
Each of R¹, R² and R³ is independently selected from the group consisting of hydrogen, blocking groups, capping groups, labels, linking groups, bonds to adjacent units and groups of the formula

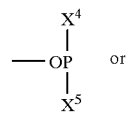

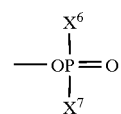

wherein
X⁴ is halogen or substituted amino,
X⁵ is alkyl, alkoxy, aryloxy, or a cyano derivative thereof,
X⁶ is halogen, amino or O, and $X^7$ is alkyl, alkoxy or aryloxy, or may be H only if $X^6$ is O, with the proviso that at least one of $R^1$, $R^2$ and $R^3$ is not hydrogen;

Each of $X^1$, $X_2$, and $X^3$ is independently selected from the group consisting of compounds of the formula $$-X_r-Y^4-$$

where r is an integer at least 1, each X is independently C or O, and each C can independently be substituted or unsubstituted, saturated or unsaturated, and $Y^4$ is selected from the group consisting of, O, S, NH, N=N and a direct bond linking $X_r$ with $R^1$, $R^2$, or $R^3$; and Each of $Y^1$, $Y^2$, and $Y^3$ is independently O or S, said non-nucleotide unit bound to at least one nucleotide monomeric unit by a bond or linking group at either $R^1$, $R^2$ or $R^3$.

18. A method for preparing a nucleic acid oligomer having both nucleotide and non-nucleotide units, comprising
coupling at least one unit comprising a compound of the formula:

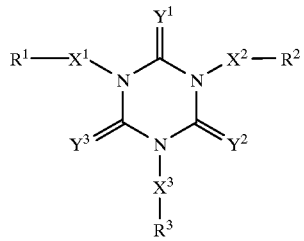

wherein

Each of $R^1$, $R^2$ and $R^3$ is independently selected from the group consisting of hydrogen, blocking groups, capping groups, labels, linking groups, bonds to adjacent units, and groups of the formula (a)

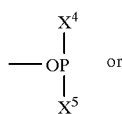

or (b)

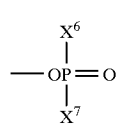

wherein $X^4$ is halogen or substituted amino, $X^5$ is alkyl, alkoxy, aryloxy, or a cyano derivative thereof, $X^6$ is halogen, amino or O, and $X^7$ is alkyl, alkoxy or aryloxy, or may be H only if $X^6$ is O, with the proviso that at least one of $R^1$, $R^2$ and $R^3$ is not hydrogen;

Each of $X^1$, $X_2$, and $X^3$ is independently selected from the group consisting of compounds of the formula $$-X_r-Y^4-$$

where r is an integer at least 1, each X is independently C or O, and each C can independently be substituted or unsubstituted, saturated or unsaturated, and $Y^4$ is selected from the group consisting of, O, S, NH N=N and a direct bond linking $X_r$ with $R^1$, $R^2$, or $R^3$; and Each of $Y^1$, $Y^2$, and $Y^3$ is independently O or S, to at least one nucleotide unit by a bond or linking group at either $R^1$, $R^2$ or $R^3$.

19. A method as recited in claim 18 further comprising attaching at least one detectable label to at least one of $R^1$, $R^2$ and $R^3$.

20. A kit for preparing a nucleic acid oligomer having both nucleotide and non-nucleotide units, comprising
a receptacle adapted to hold one or more individual reagent containers; and
a first container containing a reagent in accordance with the formula:

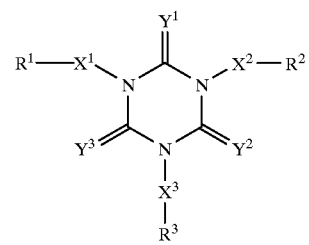

wherein

Each of $R^1$, $R^2$ and $R^3$ is independently selected from the group consisting of hydrogen, blocking groups, capping groups, labels, and groups of the formula (a)

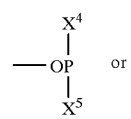

or (b)

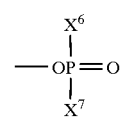

wherein $X^4$ is halogen or substituted amino, $X^5$ is alkyl, alkoxy, aryloxy, or a cyano derivative thereof, $X^6$ is halogen, amino or O, and $X^7$ is alkyl, alkoxy or aryloxy, or may be H only if $X^6$ is O, with the proviso that at least one of $R^1$, $R^2$ and $R^3$ is not hydrogen;

Each of $X^1$, $X_2$, and $X^3$ is independently selected from the group consisting of compounds of the formula $$-X_r-Y^4-$$

where r is an integer at least 1, each X is independently C or O, and each C can independently be substituted or unsubstituted, saturated or unsaturated, and $Y^4$ is selected from the group consisting of, O, S, NH, N=N and a direct bond linking $X_r$ with $R^1$, $R^2$, or $R^3$; and Each of $Y^1$, $Y^2$, and $Y^3$ is independently selected from the group consisting of O and S.

21. A kit as recited in claim 20, further comprising a second container containing (1) a reagent used in the synthesis of oligomers, or (2) a reagent used in the detection of a functional moiety associated with said reagent.

22. A kit as recited in claim 20, further comprising a second container containing a reagent used in connection with a functional moiety selected from the group consisting of detectable labels, intercalating agents, metal chelators, drugs, hormones, proteins, peptides, free radical generators, nucleolytic agents, proteolytic agents, catalysts, specific binding agents, agents which modify DNA transport across a biological barrier, and substances which alter the solubility of a nucleotide oligomer.

23. A method for detecting the presence or amount of an analyte in a sample comprising providing a sample suspected of containing an analyte of interest;

providing a nucleic acid oligomer having both nucleotide and non-nucleotide units, at least one of said non-nucleotide units comprising a compound of the formula:

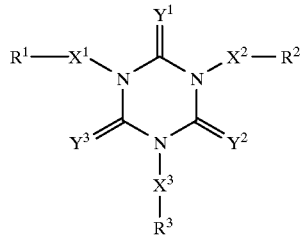

wherein

Each of $R^1$, $R^2$ and $R^3$ is independently selected from the group consisting of hydrogen, blocking groups, capping groups, labels, linking groups, bonds to adjacent units, and groups of the formula

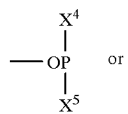  (a)

or

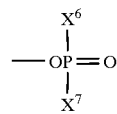  (b)

wherein
$X^4$ is halogen or substituted amino,
$X^5$ is alkyl, alkoxy, aryloxy, or a cyano derivative thereof,
$X^6$ is halogen, amino or O, and
$X^7$ is alkyl, alkoxy or aryloxy, or may be H only if $X^6$ is O, with the proviso that at least one of $R^1$, $R^2$ and $R^3$ further comprises a detectable label, Each of $X^1$, $X^2$, and $X^3$ is independently selected from the group consisting of compounds of the formula
where r is an integer at least 1, each X is independently C or O, and each C can independently be substituted or unsubstituted, saturated or unsaturated, and $Y^4$ is selected from the group consisting of, O, S, NH, N=N and a direct bond linking $X_r$ with $R^1$, $R^2$, or $R^3$; and Each of $Y^1$, $Y^2$, and $Y^3$ is independently O or S, said non-nucleotide unit bound to at least one nucleotide monomeric unit by a bond or a linking group at either $R^1$, $R^2$ or $R^3$, and wherein said oligomer is configured so as to be able to hybridize with said analyte;

exposing said sample to said oligomer for a time and under conditions which permit said oligomer to hybridize with any analyte present in said sample; and detecting the presence or amount of said analyte in said sample.

24. A method as recited in claim 23, wherein said oligomer is bound to a solid support selected from the group consisting of glass beads, microbeads, resins, polystyrene, membranes, and microtiter plates.

25. A method as recited in claim 24, wherein said solid support comprises controlled pore glass.

26. A method as recited in claim 24, wherein said solid support comprises a microtiter plate.

* * * * *